(12) United States Patent
Ohler et al.

(10) Patent No.: US 10,183,901 B2
(45) Date of Patent: Jan. 22, 2019

(54) STABILIZATION AND HYDROGENATION METHODS FOR MICROBIAL-DERIVED OLEFINS

(71) Applicant: AMYRIS, INC., Emeryville, CA (US)

(72) Inventors: Nicholas L. Ohler, San Leandro, CA (US); Roberto Vazquez, Kensington, CA (US)

(73) Assignee: AMYRIS, INC., Emeryville, CA (US)

( * ) Notice: Subject to any disclaimer, the term of this patent is extended or adjusted under 35 U.S.C. 154(b) by 120 days.

(21) Appl. No.: 15/458,907

(22) Filed: Mar. 14, 2017

(65) Prior Publication Data

US 2017/0283346 A1 Oct. 5, 2017

Related U.S. Application Data

(60) Continuation of application No. 13/951,137, filed on Jul. 25, 2013, now Pat. No. 9,611,189, which is a
(Continued)

(51) Int. Cl.
*C07C 1/00* (2006.01)
*C07C 5/03* (2006.01)
(Continued)

(52) U.S. Cl.
CPC .................. *C07C 5/03* (2013.01); *C07C 7/20* (2013.01); *C07C 11/21* (2013.01); *C10G 45/00* (2013.01);
(Continued)

(58) Field of Classification Search
USPC ...................................... 585/240–242; 44/305
See application file for complete search history.

(56) References Cited

U.S. PATENT DOCUMENTS 3,702,348 A 11/1972 Nehring et al.
4,968,612 A 11/1990 Hsieh
(Continued)

FOREIGN PATENT DOCUMENTS

GB 1297768 11/1972
WO WO 2006/108698 10/2006
(Continued)

OTHER PUBLICATIONS

International Preliminary Report on Patentability for PCT/US2010/029774, dated Jan. 18, 2012, 6 pages.
(Continued)

*Primary Examiner* — Nina Bhat
(74) *Attorney, Agent, or Firm* — Squire Patton Boggs (US) LLP

(57) ABSTRACT

Methods and compositions for stabilization and subsequent hydrogenation of a microbial-derived immiscible olefin are described. The methods comprise separating immiscible olefin from a mixture comprising an aqueous solution, microbial cells and immiscible olefin thereby forming a crude olefin composition; purifying the crude olefin composition thereby forming a purified olefin composition; and adding a phenolic antioxidant to the purified olefin composition wherein the phenolic antioxidant is a phenol derivative containing an unfused phenyl ring with one or more hydroxyl substituents. The methods further comprise reacting the purified olefin composition with hydrogen in the presence of a hydrogen catalyst such that hydrogen saturates at least one double bond in the olefin. Hydrogenated compositions produced by the methods are further provided.

20 Claims, 10 Drawing Sheets

Related U.S. Application Data division of application No. 12/753,413, filed on Apr. 2, 2010, now Pat. No. 8,519,204.

(60) Provisional application No. 61/249,900, filed on Oct. 8, 2009, provisional application No. 61/166,185, filed on Apr. 2, 2009.

(51) Int. Cl.

| | | |
|---|---|---|
| *C07C 7/20* | (2006.01) | |
| *C07C 11/21* | (2006.01) | |
| *C10G 45/00* | (2006.01) | |
| *C10G 53/04* | (2006.01) | |
| *C10G 53/08* | (2006.01) | |
| *C10G 67/04* | (2006.01) | |
| *C10G 67/06* | (2006.01) | |
| *C10L 1/04* | (2006.01) | |
| *C10L 1/16* | (2006.01) | |
| *C10L 1/183* | (2006.01) | |

(52) U.S. Cl.

CPC ............. *C10G 53/04* (2013.01); *C10G 53/08* (2013.01); *C10G 67/04* (2013.01); *C10G 67/06* (2013.01); *C10L 1/04* (2013.01); *C07C 2523/44* (2013.01); *C07C 2523/755* (2013.01); *C10G 2300/1011* (2013.01); *C10G 2300/1055* (2013.01); *C10G 2300/201* (2013.01); *C10G 2300/4081* (2013.01); *C10G 2300/802* (2013.01); *C10G 2400/22* (2013.01); *C10L 1/1608* (2013.01); *C10L 1/1832* (2013.01); *Y02P 30/20* (2015.11)

(56) References Cited

U.S. PATENT DOCUMENTS

| | | | | |
|---|---|---|---|---|
| 5,151,172 | A | | 9/1992 | Kukes et al. |
| 5,379,767 | A | | 1/1995 | Derby et al. |
| 6,403,844 | B1 | | 6/2002 | Zhang et al. |
| 7,399,323 | B2 * | | 7/2008 | Renninger ............ C10L 1/1608 44/385 |
| 7,589,243 | B1 | | 9/2009 | Ryder |
| 7,846,222 | B2 | | 12/2010 | Renninger et al. |
| 7,854,774 | B2 | | 12/2010 | Renninger et al. |
| 8,173,410 | B2 * | | 5/2012 | Bott ........................ C12N 9/88 435/167 |
| 8,519,204 | B2 * | | 8/2013 | Ohler ........................ C07C 5/03 585/240 |
| 8,598,396 | B2 | | 12/2013 | Beadle et al. |
| 9,611,189 | B2 * | | 4/2017 | Ohler ........................ C07C 5/03 |
| 2002/0107423 | A1 * | | 8/2002 | Miyamoto .............. C08C 19/02 585/250 |
| 2008/0038805 | A1 * | | 2/2008 | Melis ....................... C12N 9/88 435/167 |
| 2008/0274523 | A1 * | | 11/2008 | Renninger .............. C12P 5/007 435/157 |
| 2009/0031617 | A1 * | | 2/2009 | O'Rear .................. C10G 45/06 44/308 |
| 2009/0047721 | A1 * | | 2/2009 | Trimbur ................. C10L 1/026 435/167 |
| 2009/0084025 | A1 | | 4/2009 | Bhatia et al. |
| 2010/0267971 | A1 * | | 10/2010 | Ohler ........................ C07C 5/03 549/512 |
| 2010/0330642 | A1 * | | 12/2010 | Ridley .................... C12P 5/026 435/167 |
| 2011/0203168 | A1 | | 8/2011 | Franklin et al. |
| 2013/0310615 | A1 | | 11/2013 | Ohler et al. |

FOREIGN PATENT DOCUMENTS

| | | |
|---|---|---|
| WO | WO 2007/139924 | 12/2007 |
| WO | WO 2007/140339 | 12/2007 |
| WO | WO 2008/045555 | 4/2008 |
| WO | WO 2008/113041 | 9/2008 |
| WO | WO 2008/133658 | 11/2008 |
| WO | WO 2008/140492 | 11/2008 |
| WO | WO 2008/151149 | 12/2008 |
| WO | WO 2009/014636 | 1/2009 |

OTHER PUBLICATIONS

International Search Report for PCT/US2010/029774 dated May 25, 2011, 17 pages.

Ramaiah et al., The Journal of Organic Chemistry, (1995), vol. 60, No. 19, pp. 6211-6213.

Response to Written Opinion of the International Preliminary Examining Authority, dated Nov. 16, 2011, 9 pages.

* cited by examiner

STABILIZATION AND HYDROGENATION METHODS FOR MICROBIAL-DERIVED OLEFINS

RELATED APPLICATIONS

This application is a continuation application of U.S. application Ser. No. 13/951,137 filed Jul. 25, 2013, now U.S. Pat. No. 9,611,189, which is a divisional application of U.S. application Ser. No. 12/753,413 filed Apr. 2, 2010, now U.S. Pat. No. 8,519,204, which claims priority to U.S. provisional application nos. 61/166,185 filed Apr. 2, 2009 and 61/249,900 filed Oct. 8, 2009. The disclosures of the above referenced applications are incorporated by reference herein in their entireties.

FIELD

Provided herein are processes and systems for stabilization and subsequent hydrogenation of microbial-derived olefins.

BACKGROUND

Petroleum-derived compounds and compositions are found in a variety of products ranging from plastics to household cleaners as well as fuels. Given the environmental impact of these compositions, there is an increasing demand for more renewable and sustainable alternatives.

With recent advances in metabolic engineering, biology is providing viable alternatives to petroleum-derived compounds and compositions. For example, isoprenoids comprise a diverse class of compounds with over 50,000 members, and have a variety of uses including as specialty chemicals, pharmaceuticals and even fuels. Most isoprenoid compounds conventionally have been synthesized from petroleum sources or extracted from plant sources. Now, a third option exists which is capable of making a desired isoprenoid compound using microbial cells. Systems for making petroleum-derived compounds and compositions have been described, for example, by U.S. Pat. No. 7,399,323; U.S. Patent Publication No. 2008/0274523; and PCT Publication Nos. WO 2007/140339, WO 2008/140492, WO 2008/133658, and WO 2009/014636.

However, in order for a microbial-derived compound to be competitive, it should be made more cost effectively than a comparable compound obtained from naturally occurring sources. As a result, methods for obtaining the most optimal yield of a desired compound are needed. Such methods are provided herein.

SUMMARY

Provided herein is a method of stabilizing a microbial-derived olefin comprising separating immiscible olefin from a mixture comprising an aqueous solution, microbial cells and immiscible olefin thereby forming a crude olefin composition; purifying the crude olefin composition thereby forming a purified olefin composition; and adding a phenolic antioxidant to the purified olefin composition to form a stabilized purified microbial-derived olefin composition. In certain embodiments, the purification step is selected from fractional distillation, flash distillation, adsorption, liquid chromatography, solvent extraction and a combination thereof. In certain embodiments, the immiscible olefin comprises farnesene.

In another aspect, provided herein is a stabilized microbial olefin composition comprising an immiscible olefin in an amount at least about 93% by weight of the composition; and a phenolic antioxidant in an amount at least about 0.0001% by weight of the composition. In one embodiment, a stabilized microbial olefin composition comprises an immiscible olefin in an amount at least about 93% by weight of the composition; and a phenolic antioxidant in an amount from about 0.0001-0.5% by weight of the composition. In one embodiment, a stabilized microbial olefin composition comprises an immiscible olefin in an amount at least about 93% by weight of the composition; and a phenolic antioxidant in an amount from about 0.0001-0.1%, 0.0005-0.1%, 0.0005-0.01%, 0.0005-0.05 or 0.001 to 0.01% by weight of the composition. In another aspect, provided herein is a stabilized microbial olefin composition comprising an immiscible olefin in an amount at least about 93% by weight of the composition; and a phenolic antioxidant in an amount at least about 0.001% by weight of the composition.

In certain embodiments, provided herein is a method for hydrogenation of an immiscible olefin comprising reacting an immiscible olefin with hydrogen in the presence of a hydrogenation catalyst such that hydrogen saturates at least one double bond in the immiscible olefin and wherein the hydrogenation reaction occurs at room temperature or higher temperature. In certain embodiments, the hydrogenation reaction provided herein occurs a temperature that is 20° C. or greater. In certain embodiments, the hydrogenation reaction provided herein occurs a temperature of about 20° C., 30° C., 40° C., 50° C., 60° C., 70° C., 80° C., 90° C., 100° C. or greater. In certain embodiments, the hydrogenation reaction provided herein occurs a temperature from about 20-100° C., 40-100° C., 50-100° C., 75-100° C., 90-100° C., 90-125° C., 80-125° C. or greater. In certain embodiments, provided herein is a method for hydrogenation of an immiscible olefin comprising reacting an immiscible olefin with hydrogen in the presence of a hydrogenation catalyst such that hydrogen saturates at least one double bond in the immiscible olefin and wherein the hydrogenation reaction occurs at a temperature greater than about 100° C. In certain embodiments, the hydrogenation reaction is conducted in a fixed bed reactor.

In one aspect, provided herein is a method for hydrogenating an immiscible olefin comprising: a) providing a feed stream to the inlet of a fixed bed reactor wherein the feed stream comprises an immiscible olefin and a diluent composition; b) contacting the feed stream with hydrogen in the presence of a hydrogenation catalyst at a temperature greater than about 100° C. thereby producing an effluent; c) separating the effluent which comprises a hydrogenated immiscible olefin into a product stream comprising a hydrogenated immiscible olefin and a recycle stream comprising a hydrogenated immiscible olefin; d) adding the recycle stream as part of the diluent composition to a stream comprising the immiscible olefin to form a feed stream comprising recycled hydrogenated immiscible olefin; e) providing the feed stream comprising recycled hydrogenated immiscible olefin to the inlet of the fixed bed reactor; and f) repeating steps b)-e) at least once.

In certain embodiments, provided herein is a purified farnesene composition comprising a microbial-derived mixture comprising farnesene in an amount that is equal to or greater than about 93% by weight and the following compounds each of which is present in an amount that is equal to or greater than about 0.1% by weight: bisabolene, zingiberene, farnesol, and farnesene epoxide; and a phenolic antioxidant in an amount that is at least about 0.001% by weight.

In certain embodiments, provided herein are processes and systems for catalytic hydrogenation of farnesene to obtain farnesane. In one aspect, provided herein is a process for hydrogenation of farnesene by contacting a farnesene feed and hydrogen with a catalyst.

DETAILED DESCRIPTION

Terminology

Figure 1:
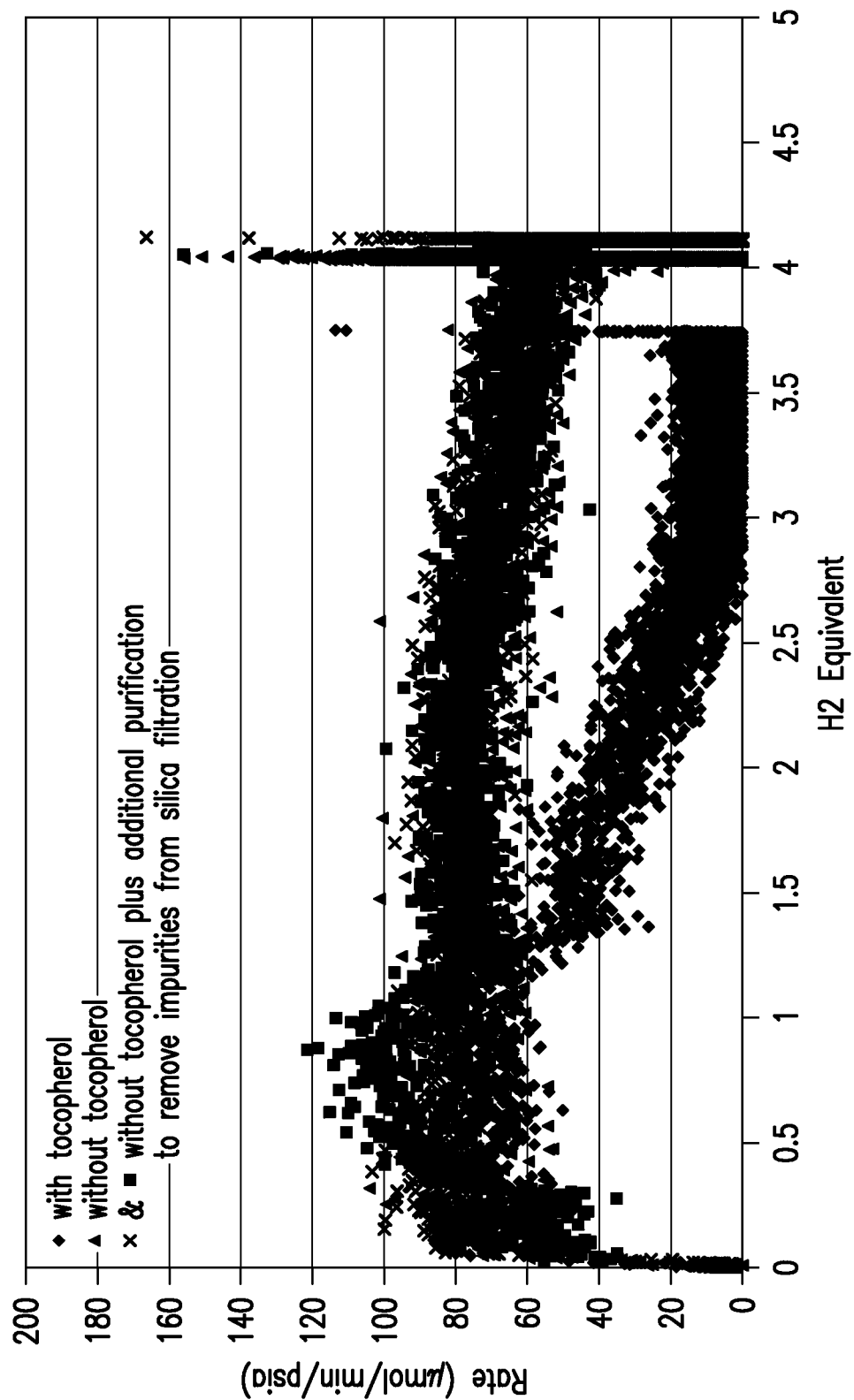
FIG. 1 is a plot of the rate of hydrogenation versus hydrogen equivalents during a hydrogenation reaction of commercially available trans-β farnesene (Bedoukian Research). In the plot, data for hydrogenation of trans-β farnesene with α-tocopherol is represented by ♦, data for hydrogenation of trans-β farnesene without α-tocopherol is represented by ▲, and data for hydrogenation of trans-β farnesene without α-tocopherol plus additional purification from silica filtration to remove impurities is represented by x and ■, respectively. The rate of observed hydrogenation as a function of hydrogen equivalent appears to be limited by the α-tocopherol added by Bedoukian to stabilize farnesene.

As used herein, "microbial-derived olefin" refers a compound with at least one double bound that is made by microbial cells (both recombinant as well as naturally occurring). In certain embodiments, the microbial-derived olefin is a hydrocarbon with at least one carbon-carbon double bond. In certain embodiments, the microbial-derived olefin is an isoprenoid. In certain embodiments, the microbial-derived olefin is a $C_5$-$C_{20}$ isoprenoid. In certain embodiments, the microbial-derived olefin is a $C_{10}$-$C_{15}$ isoprenoid. In further embodiments, the microbial-derived olefin is an isoprenoid with at least one carbon-carbon double bond. In additional embodiments, the microbial-derived olefin is a $C_5$-$C_{20}$ isoprenoid or a $C_{10}$-$C_{15}$ isoprenoid with at least one carbon-carbon double bond.

As used herein, "immiscible olefin" refers to a microbial-derived olefin that is immiscible with water.

As used herein, "crude olefin composition" refers to a composition comprising an immiscible olefin wherein the olefin is present in the composition in an amount greater than about 50% by weight but is less than about 92% by weight.

As used herein, "purified olefin composition" refers to a composition comprising an immiscible olefin wherein the olefin is present in the composition in an amount equal to or greater than about 93% by weight. In certain embodiments, the olefin is present in an amount equal to or greater than about 95% by weight.

As used herein, "stabilized purified olefin composition" refers to a composition comprising a purified olefin composition and a phenolic antioxidant.

As used herein, "phenolic antioxidant" refers to an antioxidant that is a phenol or a phenol derivative, wherein the phenol derivative contains an unfused phenyl ring with one or more hydroxyl substitutents. The term also includes polyphenols. Illustrative examples of a phenolic antioxidant include: resveratrol; 3-tert-butyl-4-hydroxyanisole; 2-tert-butyl-4-hydroxyanisole; 4-tert-butylcatechol (which is also known as TBC); 2,4-dimethyl-6-tert-butylphenol; and 2,6-di-tert-butyl-4-methylphenol (which is also known as butyl-hydroxytoluene or BHT). Additional examples of phenolic antioxidants are disclosed in U.S. Pat. No. 7,179,311.

As used herein, "hydrogenated immiscible olefin" refers to a partially hydrogenated immiscible olefin. In other words, an immiscible olefin that had a plurality of double bonds wherein at least one of its double bonds has been hydrogenated leaving at least one double bond remaining.

As used herein, "saturated immiscible olefin" refers to a fully hydrogenated counterpart of an immiscible olefin.

"α-Farnesene" refers to a compound having the following structure:

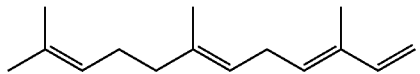

or an isomer thereof. In certain embodiments, the α-farnesene comprises a substantially pure isomer of α-farnesene. In certain embodiments, the α-farnesene comprises a mixture of isomers, such as cis-trans isomers. In further embodiments, the amount of each of the isomers in the α-farnesene mixture is independently from about 0.1 wt. % to about 99.9 wt. %, from about 0.5 wt. % to about 99.5 wt. %, from about 1 wt. % to about 99 wt. %, from about 5 wt. % to about 95 wt. %, from about 10 wt. % to about 90 wt. %, from about 20 wt. % to about 80 wt. %, based on the total weight of the α-farnesene mixture.

"β-Farnesene" refers to a compound having the following structure:

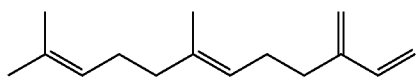

or an isomer thereof. In certain embodiments, the β-farnesene comprises a substantially pure isomer of β-farnesene. In certain embodiments, the β-farnesene comprises a mixture of isomers, such as cis-trans isomers. In further embodiments, the amount of each of the isomers in the β-farnesene mixture is independently from about 0.1 wt. % to about 99.9 wt. %, from about 0.5 wt. % to about 99.5 wt. %, from about 1 wt. % to about 99 wt. %, from about 5 wt. % to about 95 wt. %, from about 10 wt. % to about 90 wt. %, from about 20 wt. % to about 80 wt. %, based on the total weight of the β-farnesene mixture.

"Farnesene" refers to α-farnesene, β-farnesene or a mixture thereof.

"Hydrogenated farnesene" refers to α-farnesene, β-farnesene or a mixture thereof wherein at least one double bond is hydrogenated. Thus, hydrogenated farnesene emcompasses, for example, α-farnesene wherein one, two, three or four double bonds are hydrogenated, β-farnesene wherein one, two, three or four double bonds are hydrogenated, and a mixture thereof. Hydrogenated farnesene is obtained by partial hydrogenation of farnesene.

"Farnesane" refers to a compound having structure:

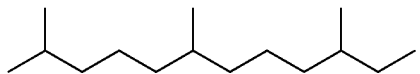

or a stereoisomer thereof. In certain embodiments, the farnesane comprises a substantially pure stereoisomer of farnesane. In certain embodiments, the farnesane comprises a mixture of stereoisomers, such as enantiomers and diastereoisomers, of farnesane. In further embodiments, the amount of each of the stereoisomers in the farnesane mixture is independently from about 0.1 wt. % to about 99.9 wt. %, from about 0.5 wt. % to about 99.5 wt. %, from about 1 wt. % to about 99 wt. %, from about 5 wt. % to about 95 wt. %, from about 10 wt. % to about 90 wt. %, from about 20 wt. % to about 80 wt. %, based on the total weight of the farnesane mixture.

As used herein, "unsaturated farnesane" refers to one or more farnesane molecules containing one or more double bonds. For example, monounsaturated farnesane refers to one or more farnesane molecules containing one double bond. Unsaturated farnesane is obtained by partial hydrogenation of farnesane.

"Farnesene epoxide refers to a compound having structure:

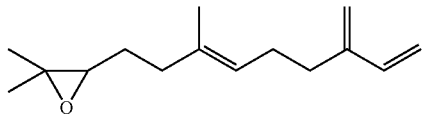 [SMILES: C=CC(=C)CC/C=C(\C)CCC1OC1(C)C]

or an isomer thereof.

"Farnesol refers to a compound having the structure:

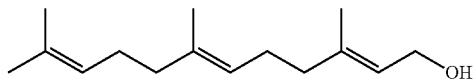 [SMILES: CC(C)=CCC/C(C)=C/CC/C(C)=C/CO]

or an isomer thereof.

"Limonene" refers to a compound having the structure

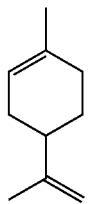

or an isomer thereof.

"Zingiberene" refers to a compound having the following structure:

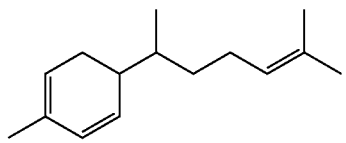

or an isomer thereof.

"Bisabolene" refers to a compound having the following structure:

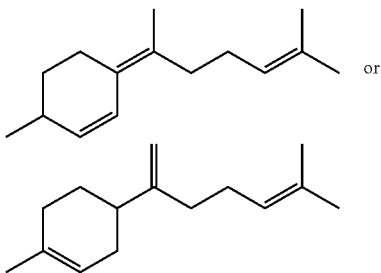

or an isomer thereof.

"Bisabolane" refers to a compound having the following structure:

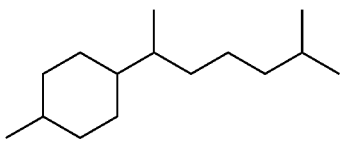

or an isomer thereof.

As used herein, "farnesene feed" refers to a mixture of farnesene and a diluent, such as farnesane.

As used herein, "product fraction" refers to a fraction of a product composition comprising a hydrogenated immiscible olefin, such as hydrogenated farnesene, that is separated from an effluent of a hydrogenation reaction provided herein. Optionally, the product fraction can undergo further hydrogenation in a secondary reactor to remove residual unsaturation to obtain a saturated product, e.g., farnesane, or can be used without further hydrogenation, for example in biofuels, without further treatment.

As used herein, "reactant stream" refers to a mixture of an immiscible olefin feed and hydrogen.

As used herein and unless otherwise indicated, the term "process(es)" refers to method(s) disclosed herein that is (are) useful for hydrogenation of a microbial-derived olefin where at least one double bond of the olefin is converted into a single bond by the addition of hydrogen. Modifications to the methods disclosed herein (e.g., starting materials, reagents, temperatures, pressure) are also encompassed.

As used herein, "recycling fraction" refers to a fraction of a product composition that is separated from an effluent of a hydrogenation reaction provided herein and recycled as a diluent in the hydrogenation reaction.

As used herein and unless otherwise indicated, a reaction that is "substantially complete" or is driven to "substantial completion" means that the reaction contains more than about 80% desired product by percent yield, more than about 90% desired product by percent yield, more than about 95% desired product by percent yield, or more than about 97% desired product by percent yield.

As used herein, "axial temperature rise" refers to the increase in temperature during a hydrogenation reaction in a cocurrent downflow reactor as a reactant stream flows from the top of the reactor to the bottom of the reactor in presence of a catalyst.

In the following description, all numbers disclosed herein are approximate values, i regardless whether the word "about" or "approximate" is used in connection therewith. Numbers may vary by 1 percent, 2 percent, 5 percent, or, sometimes, 10 to 20 percent. Whenever a numerical range with a lower limit, $R^L$, and an upper limit, $R^U$, is disclosed, any number falling within the range is specifically disclosed. In particular, the following numbers within the range are specifically disclosed: $R=R^L+k*(R^U-R^L)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

The claimed subject matter can be understood more fully by reference to the following detailed description and illustrative examples, which are intended to exemplify non-limiting embodiments.

Stabilized Compositions of Immiscible Olefin and Methods for Making the Same

Provided herein are microbial olefin compositions and methods for stabilizing and hydrogenating the same. The microbial olefins can be made using any technique deemed suitable by one of skill in the art. Useful exemplary microbial methods for making olefinic isoprenoids are described in U.S. Pat. No. 7,399,323; U.S. Patent Publication No. 2008/0274523; and PCT Publication Nos. WO 2007/140339, WO 2008/140492, WO 2008/133658, and WO 2009/014636, all incorporated by reference in their entireties. Useful exemplary microbial methods for making fatty-acid derived olefins are described in U.S. Patent Publication No. 2009/0047721; and PCT Publication Nos. WO 2008/113041 and WO 2008/151149, all incorporated by reference in their entireties.

In one aspect provided herein is a method of stabilizing a microbial-derived olefin. In one aspect a method of stabilizing a microbial-derived olefin comprises adding a phenolic antioxidant to the microbial-derived composition.

In certain embodiments, the method comprises:
a) separating immiscible olefin from a mixture comprising an aqueous solution, microbial cells and immiscible olefin thereby forming a crude olefin composition; and
b) adding a phenolic antioxidant to the crude olefin composition to form a stabilized microbial-derived olefin composition.

In certain embodiments, the method further comprises purifying the olefin composition, before and/or after step b) to form a purified olefin composition.

In certain embodiments, the method comprises:
a) separating immiscible olefin from a mixture comprising an aqueous solution, microbial cells and immiscible olefin thereby forming a crude olefin composition;
b) purifying the crude olefin composition thereby forming a purified olefin composition; and
c) adding a phenolic antioxidant to the purified olefin composition to form a stabilized purified microbial-derived olefin composition.

In certain embodiments, the method further comprises adding a phenolic antioxidant to the crude olefin composition before the purification step. In certain embodiments, the method further comprises adding a phenolic antioxidant to the olefin composition before and after the purification step.

In certain embodiments, the method further comprises contacting the purified olefin composition with hydrogen in the presence of a hydrogenation catalyst thereby forming a hydrogenated counterpart to the immiscible olefin wherein at least one carbon-carbon double bond becomes saturated by the addition of hydrogen.

The olefin is derived from microbial cells. In certain embodiments, the microbial cells are bacteria. In certain embodiments, the microbial cells belong to the genera *Escherichia, Bacillus, Lactobacillus*. In certain embodiments, the microbial cells are *E. coli*. In further embodiments, the microbial cells are fungi. In still further embodiments, the microbial cells are yeast. In still further embodiments, the microbial cells are *Kluyveromyces, Pichia, Saccharomyces*, or *Yarrowia*. In additional embodiments, the microbial cells are *S. cerevisiae*. In certain embodiments, the microbial cells are algae. In certain embodiments, the microbial cells are *Chlorella minutissima, Chlorella emersonii, Chloerella sorkiniana, Chlorella ellipsoidea, Chlorella* sp., or *Chlorella protothecoides*.

In certain embodiments, the immiscible olefin is a hydrocarbon. In certain embodiments, the immiscible olefin is a fatty acid or a fatty acid-derivative. In further embodiments, the immiscible olefin is an isoprenoid. In still further embodiments, the immiscible olefin is a $C_5$-$C_{20}$ isoprenoid. In certain embodiments, the immiscible olefin is a $C_{10}$-$C_{15}$ isoprenoid. In additional embodiments, the immiscible olefin is selected from careen, geraniol, linalool, limonene, myrcene, ocimene, pinene, sabinene, terpinene, terpinolene, amorphadiene, farnesene, farnesol, nerolidol, valencene, and geranylgeraniol. In further additional embodiments, the immiscible olefin is myrcene, α-ocimene, β-ocimene, α-pinene, β-pinene, amorphadiene, α-farnesene or β-farnesene. In certain embodiments, the immiscible olefin is α-farnesene, β-farnesene, or a mixture thereof.

In certain embodiments, the purification step comprises fractional distillation. In certain embodiments, the purification step comprises flash distillation (which is also known as flash or partial evaporation). In certain embodiments, the purification step comprises adsorption. In certain embodiments, the purification step comprises silica gel filtration. In certain embodiments, the purification step comprises alumina treatment. In additional embodiments, the purification step comprises liquid chromatography. In further embodiments, the purification step comprises solvent extraction.

In certain embodiments, the impurities removed in the purification step include, for example, cold insolubles, such as mono-, di-, and triglycerides. When the host cells are yeast, the cold insolubles further includes ergosterol and squalene. In certain embodiments, the impurities removed in the purification step include, for example, chemicals added in upstream processing, such as antifoams, deemulsifiers and other chemicals. When the host cells are yeast, the cold insolubles further includes ergosterol and squalene.

In certain embodiments, the phenolic antioxidant is a polyphenol. In certain embodiments, the phenolic antioxidant is resveratrol. In certain embodiments, the phenolic antioxidant is a monophenol. In certain embodiments, the phenolic antioxidant is selected from: 3-tert-butyl-4-hydroxyanisole; 2-tert-butyl-4-hydroxyanisole; 2,4-dimethyl-6-tert-butylphenol; and 2,6-di-tert-butyl-4-methylphenol. In certain embodiments, the phenolic antioxidant is a catechol. In further embodiments, the phenolic antioxidant is 4-tert-butylcatechol.

In certain embodiments, the phenolic antioxidant is present in an amount that is at least about 0.0001% by weight of the composition. In certain embodiments, the phenolic antioxidant is present in an amount that is between about 0.0001% and about 0.5% by weight of the composition. In certain embodiments, the phenolic antioxidant is present in an amount that is between about 0.0001% and about 0.01% by weight of the composition. In certain embodiments, the phenolic antioxidant is present in an amount that is between about 0.0005 to 0.01%, 0.001 to 0.01%, or 0.005 to 0.01% by weight of the composition. In certain embodiments, the phenolic antioxidant is present in an amount that is at least about 0.005% by weight of the composition. In certain embodiments, the phenolic antioxidant is present in an amount that is between about 0.005% and about 0.5% by weight of the composition. In further embodiments, the phenolic antioxidant is present in an amount that is at least about 0.01% by weight of the composition. In additional embodiments, the phenolic antioxidant is present in an amount that is between about 0.05% and about 0.3% by weight of the composition. In certain embodiments, the phenolic antioxidant is present in an amount that is at least about 0.0001%, 0.0005%, 0.001%, 0.005%, 0.01%, 0.05%. 0.1% or 0.5%. In certain embodiments, the phenolic antioxidant is present in an amount that is greater than about 0.5% by weight of the composition.

In another aspect, a stabilized microbial olefin composition is provided. The composition comprises:

a) an immiscible olefin wherein the immiscible olefin is present in an amount that is equal to or greater than about 93% by weight of the composition; and b) a phenolic antioxidant wherein the phenolic antioxidant is present in an amount that is at least about 0.001% by weight of the composition.

In certain embodiments, the phenolic antioxidant is present in an amount that is at least about 0.0001% by weight of the composition. In certain embodiments, the phenolic antioxidant is present in an amount that is between about 0.0001% and about 0.5% by weight of the composition. In certain embodiments, the phenolic antioxidant is present in an amount that is between about 0.0001% and about 0.01% by weight of the composition. In certain embodiments, the phenolic antioxidant is present in an amount that is between about 0.0005 to 0.01%, 0.001 to 0.01%, or 0.005 to 0.01% by weight of the composition. In certain embodiments, the phenolic antioxidant is present in an amount that is at least about 0.005% by weight of the composition. In certain embodiments, the phenolic antioxidant is present in an amount that is between about 0.005% and about 0.5% by weight of the composition. In further embodiments, the phenolic antioxidant is present in an amount that is at least about 0.01% by weight of the composition. In additional embodiments, the phenolic antioxidant is present in an amount that is between about 0.05% and about 0.3% by weight of the composition. In certain embodiments, the phenolic antioxidant is present in an amount that is at least about 0.0001%, 0.0005%, 0.001%, 0.005%, 0.01%, 0.05%. 0.1% or 0.5%. In certain embodiments, the phenolic antioxidant is present in an amount that is greater than about 0.5% by weight of the composition.

In certain embodiments, the immiscible olefin in the composition is present in an amount that is at least about 93%, 94%, 95%, 96%, 97% or greater by weight of the composition.

In certain embodiments, the immiscible olefin in the composition comprises farnesene in an amount that is at least about 50%, 60%, 70%, 80%, 90% 93%, 95%, 97%, 99% or greater by weight of the composition.

Comparison of Chemically Synthesized and Microbial-Derived Olefins

A composition of microbial-derived olefin and a composition of its chemically synthesized counterpart can have different properties due to the different impurities contained therein. In some cases, these differences are immaterial to the desired end use. But, in certain situations, these differences can have a material impact. The methods and compositions provided herein relate to one of these situations. As it will be described more fully below, the methods and compositions can significantly decrease the hydrogenation reaction time of a microbial-derived olefin. The improvements from using the methods and processes can result in cost savings due to shorter hydrogenation times, milder reaction conditions, and longer catalyst lifetimes. Although the following focuses on the hydrogenation of farnesene for the purposes of illustration, similar results are obtained with other microbial-derived immiscible olefins.

Chemically synthesized β-farnesene was obtained from Bedoukian Research. Trans β-farnesene composition was obtained which was determined to be about 90% pure by GCMS. When this sample was hydrogenated under fairly mild hydrogenation conditions (for example, 5% Pd/C at 60 psia at 100° C.), the hydrogenation initially proceeded at a rapid rate and then the rate decreased over time as seen in FIG. 1. Several studies were conducted to determine the cause of drop in the hydrogenation rate, including studies focused on the impurities from the chemical synthesis of farnesene. Subsequently, it was finally discovered that the decrease in hydrogenation rates was due to the presence of α-tocopherol, an antioxidant added by Bedoukian Research. The amount of α-tocopherol in the commercial sample was about 0.1%.

FIG. 1 shows the plot of the rate of hydrogenation versus the hydrogen equivalents during a hydrogenation reaction of the Bedoukian 90% pure trans β-farnesene. However, when α-tocopherol is removed, for example by silica gel filtration, then the sample hydrogenated readily. A highly pure 98% β-farnesene composition as well a mixture of a mixture of α-farnesene and β-farnesene behaved similarly. In other words, if α-tocopherol was present, the hydrogenation reaction (regardless of the purity level of the farnesene sample) was impaired but if removed, the reaction proceeded readily under mild hydrogenation conditions. Because there were no significant differences between the hydrogenation behavior of a 98% β-farnesene composition versus the 90% composition or the isomeric mixture, in the discussion below the hydrogenation reaction of the commercially synthesized composition is with the 90% trans β-farnesene sample unless otherwise noted. Similarly, all samples of commercially-obtained farnesene were treated to remove α-tocopherol prior to hydrogenation unless otherwise noted.

Figure 2:
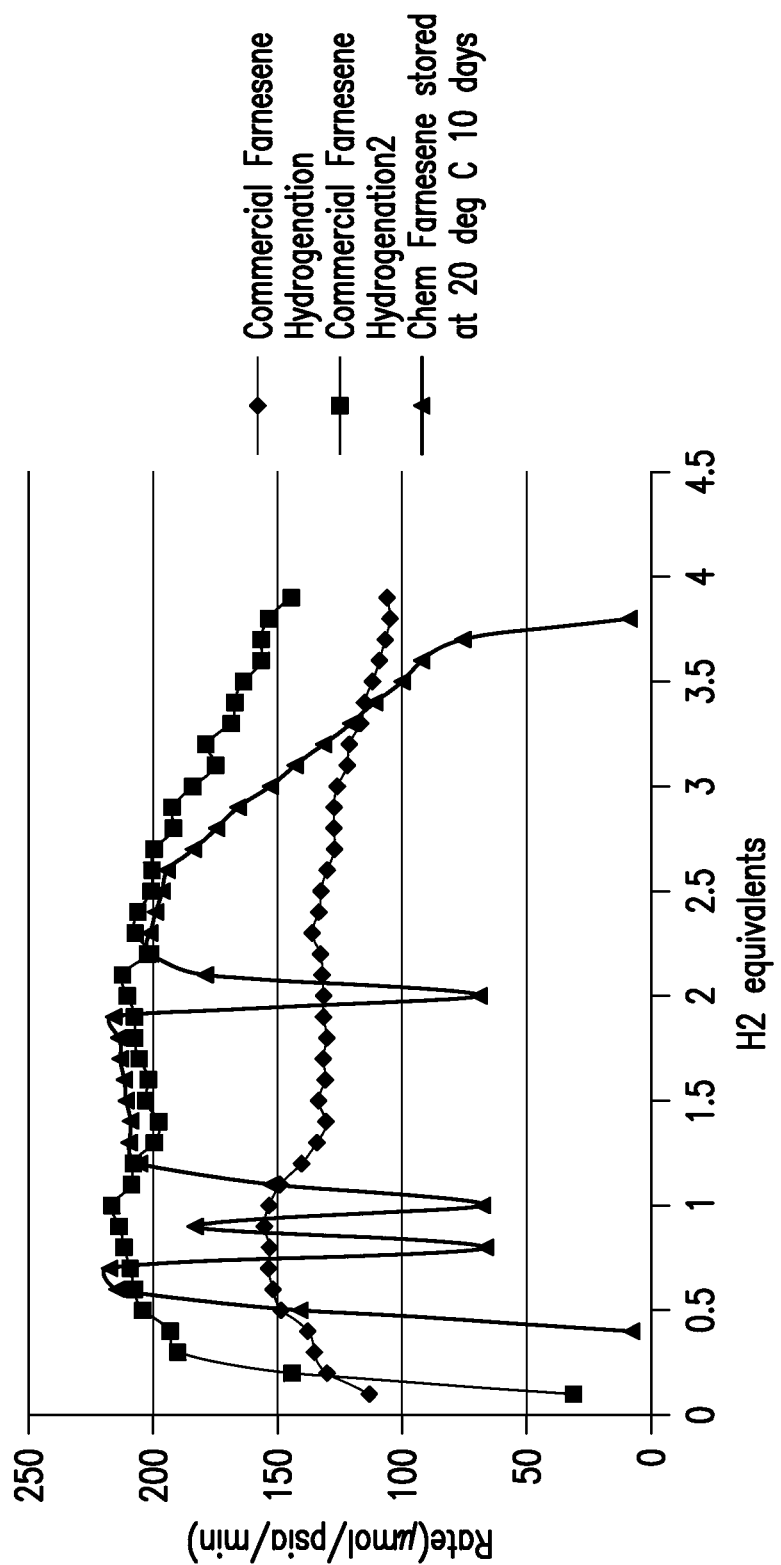
FIG. 2 is a plot comparing rate versus hydrogen equivalent for two lots of commercially available farnesene that were silica filtered to remove α-tocopherol, represented by ♦ and ■ in the plot, along with a commercially available lot of farnesene that was silica filtered to remove α-tocopherol, stored at 20° C. for ten days and then hydrogenated, represented by ▲. The hydrogenation reaction proceeded with an average value of 10.7±1.9 minutes per hydrogen equivalent (9.3 minutes per hydrogen equivalent, data represented by ♦ in the plot, and 12.1 minutes per hydrogen equivalent, data represented by ■ in the plot, individually). The hydrogenation rate of commercially available farnesene in which α-tocopherol was removed, stored at 20° C. for ten days, and then hydrogenated (data represented by ▲ in the plot) was 14.9 minutes per hydrogen equivalent. The hydrogenation conditions were 5% Pd/C at 60 psia at 100° C.

Because a potential stability issue was created from the removal of α-tocopherol from commercially-obtained farnesene, the stability of a tocopherol-free farnesene was investigated. As shown by FIG. 2, a tocopherol-free farnesene was found to be stable at 20° C. for at least 10 days. While the hydrogenation time was slightly higher (14.9 minutes per hydrogen equivalent), it was nevertheless comparable to the different lots of farnesene in which the α-tocopherol was removed just prior to hydrogenation (9.3 minutes per hydrogen equivalent and 12.1 minutes per hydrogen equivalent in two lots providing an average value of 10.7±1.9 minutes per hydrogen equivalent). The hydrogenation conditions were 5% Pd/C at 60 psia at 100° C.

With these series of experiments, a baseline for comparison (hydrogenation of commercially available farnesene with α-tocopherol removed prior to hydrogenation) was obtained. Although α-tocopherol could be removed up to ten days prior to hydrogenation, where possible, it was removed just prior to hydrogenation.

Figure 3A:
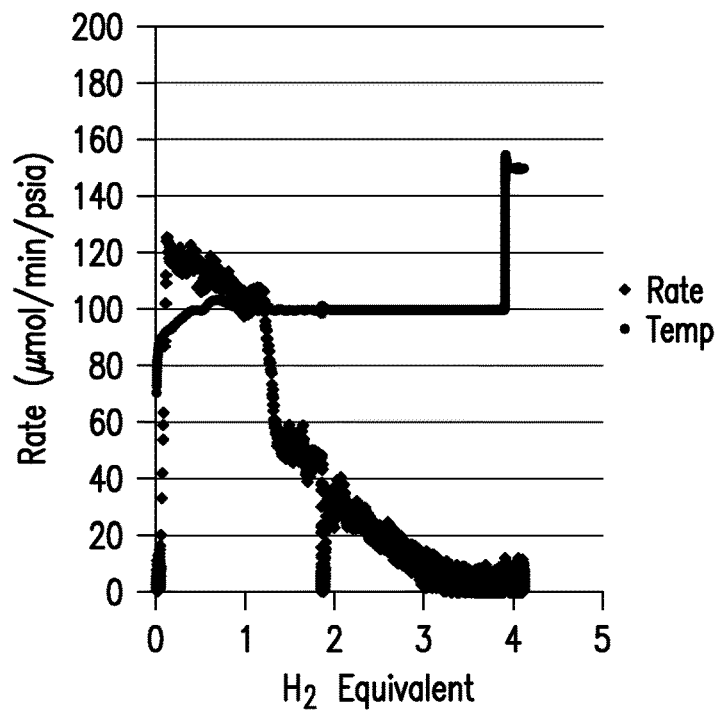
FIGS. 3A and 3B are plots of rate and temperature versus hydrogen equivalents during a hydrogenation reaction of microbially-derived farnesene and commercially available farnesene (with α-tocopherol removed), respectively, under identical reaction conditions (5% Pd/C at 60 psia at 100° C.). In the plot, data for rate is represented by ♦, data for temperature is represented by ●.
Figure 3B:
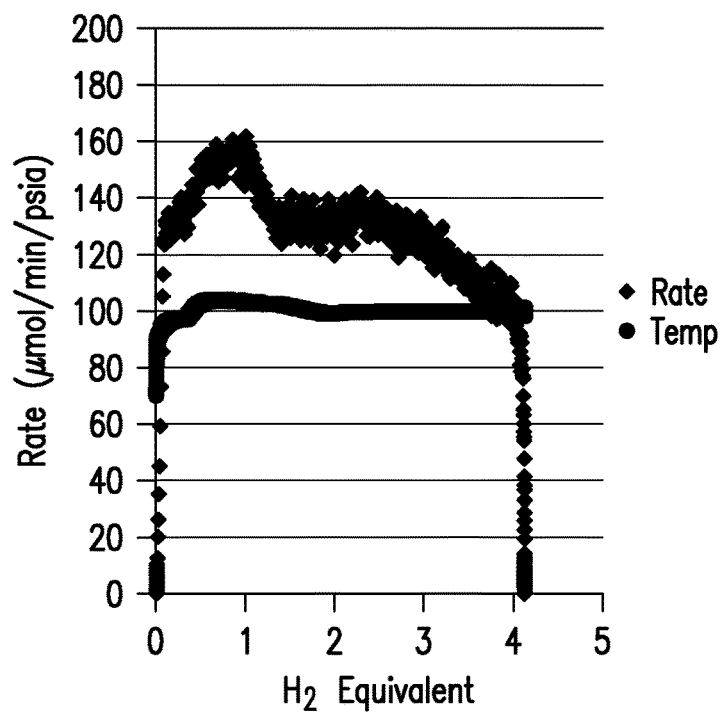

With the baseline established, microbial-derived β-farnesene (95% pure by GCMS) was hydrogenated and compared with its chemically synthesized counterpart. The results are shown in FIGS. 3A and 3B. As it can be seen in FIGS. 3A and 3B, the microbial-derived farnesene contained one or more inhibitors that impeded the progress of the hydrogenation reaction.

Figure 4:
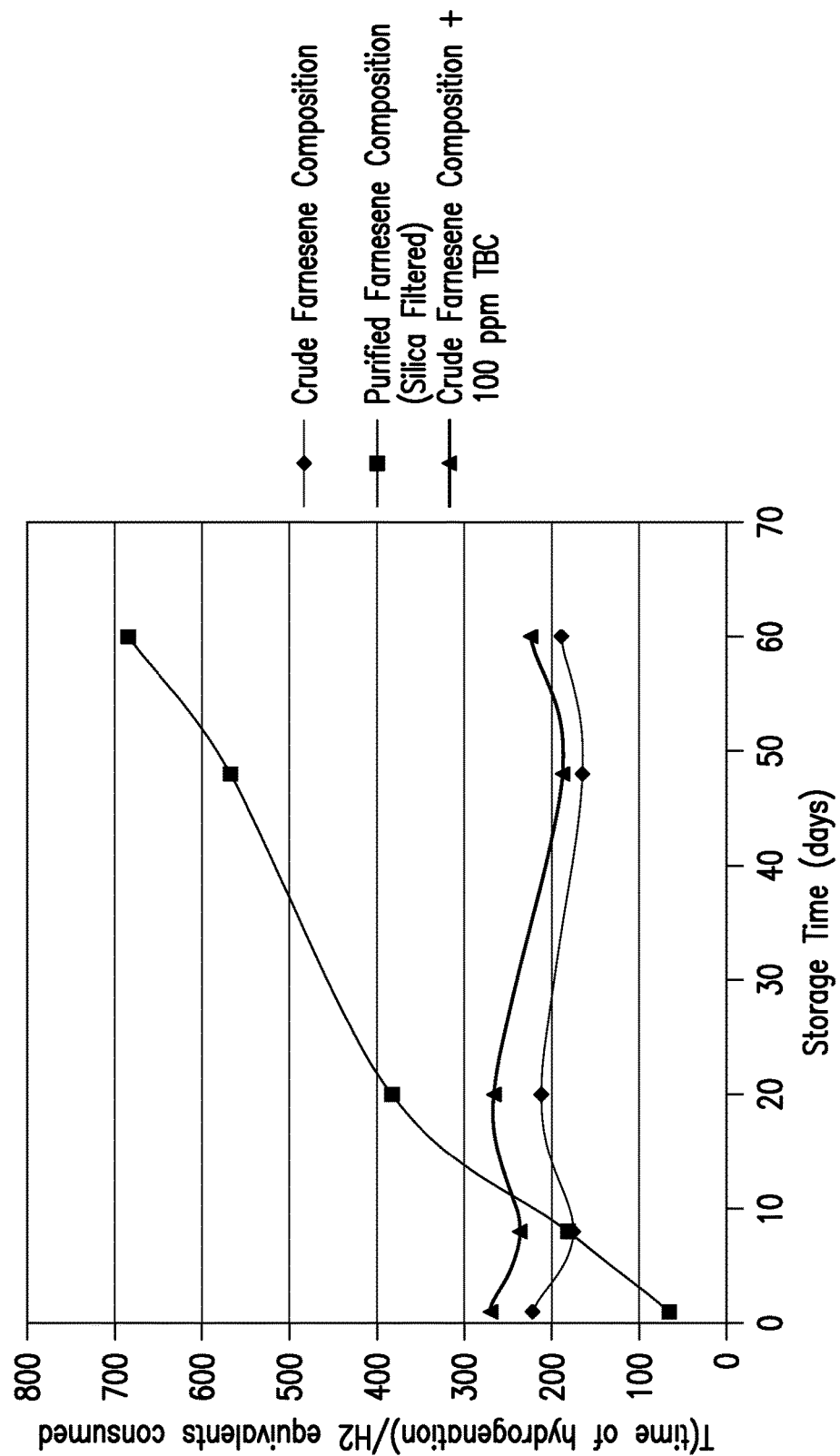
FIG. 4 is a plot showing the hydrogenation time/hydrogen equivalent versus storage time for various lots of microbial-derived farnesene at 4° C. The hydrogenation conditions were 5% Pd/C at 60 psia at 100° C. In the plot, data for crude farnesene composition is represented by ♦, data for silica filtered farnesene composition is represented by ■, and data for crude farnesene composition with 100 ppm 4-tert-butylcatechol is represented by ▲.

While efforts were made to identify the source of this inhibition in microbial-derived farnesene, a curious discovery was made. Crude microbial farnesene was found to be significantly more stable than its purified counterpart. This fact is graphically illustrated in FIG. 4. In this series of experiments, microbial-farnesene was treated in different ways and stored for up to 60 days at 4° C. FIG. 4 is a plot showing the hydrogenation times under mild hydrogenation conditions (5% Pd/C at 60 psia at 100° C.) for the various microbial farnesene as a function of storage time. Various microbial farnesene compositions used in this study were obtained as described below.

Microbial cells that were genetically modified to make farnesene were grown in culture medium, as described for example, by U.S. Pat. No. 7,399,323 and PCT Publication No. WO 2007/139924. The cells were separated from the culture medium and the resulting broth was centrifuged to purify immiscible organic layer from the aqueous medium. The resulting organic layer is the crude olefin composition wherein the immiscible olefin is present in the composition in an amount greater than about 50% by weight but is less than about 92% by weight. The crude olefin composition includes components which can precipitate from solution at cold temperatures (e.g. 4° C.). These precipitates which were termed "cold insolubles" include various glycerides such as mono-, di-, and triglycerides. When the immiscible olefin is produced in yeast, the cold insolubles also include ergosterol and squalene.

In certain embodiments, the crude olefin composition is a crude β-farnesene composition. In one aspect, removing the cells and separating the immiscible layer from the aqueous broth, yields a crude β-farnesene composition of about 90% purity by GCMS.

The crude olefin composition can be further purified to a composition comprising an immiscible olefin wherein the olefin is present in the composition in an amount equal to or greater than about 93% by weight. In certain embodiments, the olefin is present in an amount equal to or greater than about 95% by weight. Any purification method deemed suitable by one of skilled in the art can be used. In certain embodiments, the sample is further purified by distillation. In certain embodiments, the sample is further purified by flash distillation. In certain embodiments, distillation, including flash distillation is effective at removing the cold insolubles.

In certain embodiments, the sample is further purified by liquid chromatography. In further embodiments, the sample is further purified by silica filtration, alumina filtration or clay filtration. In one embodiment, the crude farnesene composition is further purified by silica filtration and the resulting purified farnesene composition is greater than 97% pure by GCMS.

As shown by FIG. 4, the crude farnesene composition is fairly stable as judged by hydrogenation times which stay relatively constant over time. In contrast, the hydrogenation times for the purified farnesene composition increases over time. However, the hydrogenation time of a recently purified farnesene composition (time 0) is similar to that of the chemically synthesized counterpart in which the α-tocopherol is removed.

The purified farnesene samples were further analyzed. In certain embodiments, these samples comprised farnesene in an amount that is equal to or greater than about 93% by weight based on GCMS. In certain embodiments, farnesene is present in an amount that is equal to or greater than about 95% by weight or, in certain embodiments equal to or greater than about 97% by weight. These purified farnesene samples further comprised the following compounds which were all in an amount that is at least about 0.05% by weight by GCMS: zingiberene (also known as ginger oil) which can be present in an amount that is equal to or greater than about 0.1%, 0.2%, 0.3%, 0.4%, 0.5%, 0.6%, or 0.7%; bisabolene which can be present in an amount that is equal to or greater than about 0.1%, 0.2%, 0.3%, 0.4%, 0.5%, 0.6%, or 0.7%; 10,11-dihydro-10,11-epoxyfarnesene which can be present in an amount that is equal to or greater than about 0.1%, 0.2%, 0.3%, 0.4%, 0.5%, 0.6%, or 0.7%; and farnesol which can be present in an amount that is equal to or greater than about 0.1%, 0.25%, 0.5%, 0.75%, 1%, 1.5%, or 2%.

Each of these components was added to a commercially obtained farnesene with α-tocopherol removed to assess impact on hydrogenation times. The hydrocarbons such as zingiberene and bisabolene had no effect on hydrogenation. Farnesol and the farnesene epoxide impeded hydrogenation only slightly at the observed concentrations (1.3 to 2 times) and thus could not account for the dramatic increases in hydrogenation times that were seen for purified farnesene compositions. Moreover, all of these components were also observed in the crude farnesene composition.

Figure 5:
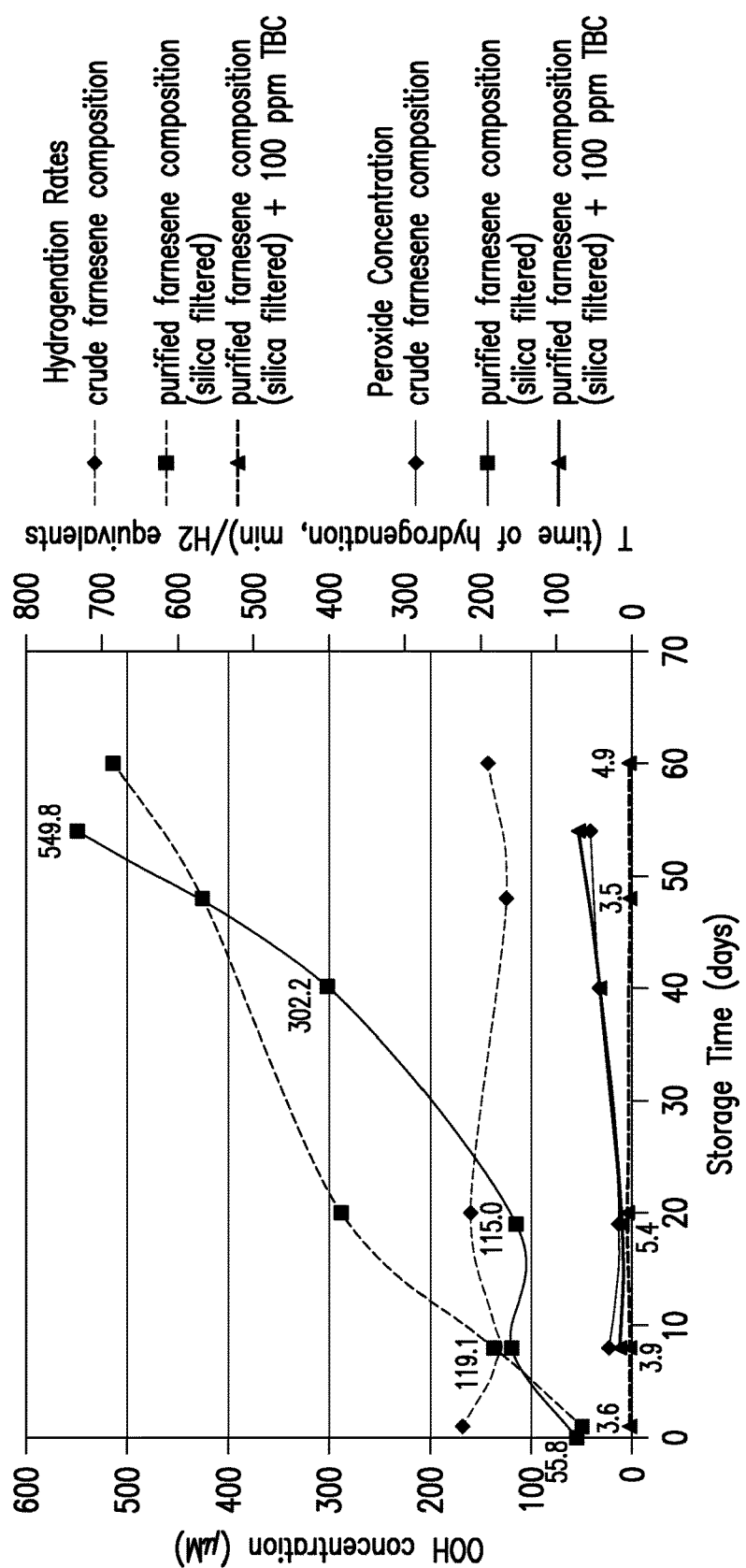
FIG. 5 is a plot showing peroxide concentration and hydrogenation time/hydrogen equivalent versus storage time for various lots of microbial-derived farnesene at 4° C. The hydrogenation conditions were 5% Pd/C at 60 psia at 100° C. In the plot, dotted lines represent hydrogenation rates and solid lines represent peroxide concentration. The data for crude farnesene composition is represented by ♦, data for silica filtered farnesene composition is represented by ■, and data for purified farnesene composition with 100 ppm 4-tert-butylcatechol is represented by ▲.

As shown by FIG. 5, the degradation in farnesene was correlated directly with peroxide concentrations which increased over time in the purified samples. Farnesene can be stabilized against peroxide formation by various antioxidants such as α-tocopherol. However, as described previously, some of the most commonly used antioxidants such as α-tocopherol have been found to inhibit hydrogenation.

In the methods and compositions provided herein, phenolic antioxidants were found to stabilize immiscible olefins without impeding any subsequent hydrogenation. Illustrative examples of phenolic antioxidants include polyphenols such as resveratrol; monophenols such as 3-tert-butyl-4-hydroxyanisole; 2-tert-butyl-4-hydroxyanisole; 2,4-dimethyl-6-tert-butylphenol; and 2,6-di-tert-butyl-4-methylphenol; and catechols such as 4-tert-butylcatechol. In certain embodiments, the addition of up to 3 weight % of a phenolic antioxidant were shown not to affect hydrogenation rates or times.

As shown in FIG. 5, the hydrogenation times of purified farnesene composition stabilized with 100 ppm of a phenolic antioxidant (100 ppm of TBC is 0.01% by weight) was comparable to that seen for the chemically synthesized counterpart in which the α-tocopherol is removed. Curiously, phenolic antioxidants such as TBC did not further improve the hydrogenation rate of a crude olefin composition. In certain embodiments, as shown by FIG. 4, the crude olefin composition appears to perform slightly better in the absence of a phenolic antioxidant than with it.

Hydrogenation

In another aspect, hydrogenation methods for microbial-derived olefins are provided. Any known hydrogenation method can be used to hydrogenate microbial-derived olefins so long as the purified olefin composition comprises a phenolic antioxidant.

In one embodiment, a method provided herein comprises:
a) obtaining an immiscible olefin; and
b) reacting the immiscible olefin with hydrogen in the presence of a hydrogenation catalyst such that hydrogen saturates at least one double bond in the immiscible olefin and wherein the hydrogenation reaction occurs at a temperature that is greater than about 100° C.

In certain embodiments, the immiscible olefin is part of a crude olefin composition. In certain embodiments, the immiscible olefin is part of a purified olefin composition. In certain embodiments, the immiscible olefin is part of a stabilized purified olefin composition.

In certain embodiments, the hydrogenation reaction occurs at a temperature equal to or greater than room temperature. In certain embodiments, the hydrogenation reaction occurs at a temperature equal to or greater than 20° C., 30° C., 40° C., 50° C., 60° C., 70° C., 80° C., 90° C., 100° C., 110° C., 120° C., 130° C., 140° C., 150° C., 160° C., 170° C., 180° C., 190° C., or 200° C. In certain embodiments, hydrogenation can occur at temperatures below 100° C. when hydrogenating an immiscible olefin. In certain embodiments, catalyst life is significantly extended if hydrogenation of an immiscible olefin is conducted above 100° C. In certain embodiments, the hydrogenation reaction occurs at a temperature equal to or greater than about 110° C., 120° C., 130° C., 140° C., 150° C., 160° C., 170° C., 180° C., 190° C., or 200° C. In certain embodiments, the hydrogenation reaction occurs at a temperature between about 110° C. and about 400° C. In certain embodiments, cracking side reactions become significant if the hydrogenation occurs at a temperature greater than about 400° C. In certain embodiments, the hydrogenation reaction occurs at a temperature between about 110° C. and about 350° C. In certain embodiments, the hydrogenation reaction occurs at a temperature between about 110° C. and about 300° C. In certain embodiments such as when hydroprocessing catalysts are used, the hydrogenation reaction occurs at a temperature between about 170° C. and about 350° C. In certain embodiments, the hydrogenation reaction occurs at a temperature between about 170° C. and about 240° C.

Figure 7:
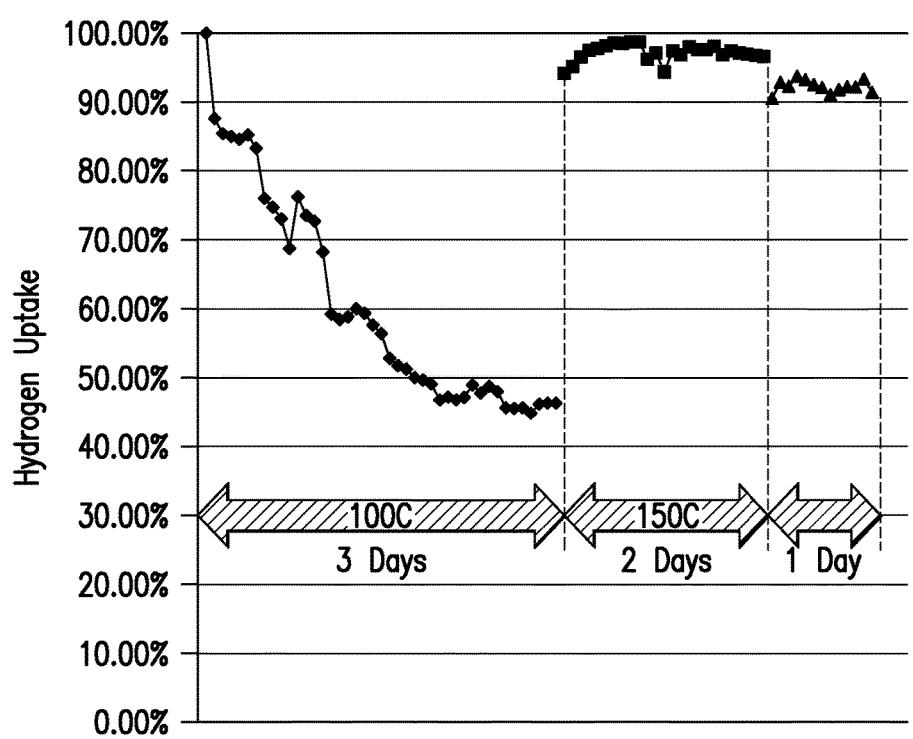
FIG. 7 is a plot of hydrogenation uptake rate for various purified olefin compositions over periods of time to test catalyst life at the process LHSV (Liquid Hourly Space Velocity) of 12 ml of olefin fed to process/mL catalyst per hour. The hydrogenation conditions were: 20% Ni/$Al_2O_3$ catalyst diluted 4× with glass beads hydrogenating a composition of 5% farnesene and 95% decane at a pressure of 500 psig. In the first part of the plot, the farnesene in the farnesene composition is a purified microbial-derived farnesene and the hydrogenation reaction occurs at 100° C. As it can be seen, the catalyst degrades rapidly over one day and continues to deactivate over three days. This catalyst could be recovered by increasing the temperature. This is shown by the second part of the plot which shows that the hydrogen uptake can be recovered almost fully by simply increasing the temperature to a temperature greater than 100° C. (in this case 150° C.). The third part of the plot demonstrates catalyst deactivation as the chemically-derived counterpart could be hydrogenated at 100° C. with no catalyst deactivation.

The benefits of performing the hydrogenation of microbial-derived olefins at temperature above 100° C. are shown in FIG. 7. To test for catalyst fouling, hydrogenation reactions were conducted at high process LHSV (Liquid Hourly Space Velocity) (process LHSV=12). Various compositions of 5% farnesene and 95% decane were hydrogenated at a pressure of 500 psig using 20% Ni/Al$_2$O$_3$ catalyst diluted 4× with glass beads. In the first part of the plot, the farnesene in the farnesene composition is a purified microbial-derived farnesene and the hydrogenation reaction occurs at 100° C. As can be seen, the catalyst can deactivate rapidly over one day and continues to deactivate over three days. However, spent catalyst can be recovered by increasing temperature to greater than 100° C. As shown by the second part of the plot, the hydrogen uptake was recovered almost fully by increasing temperature to greater than 100° C. (in this case 150° C.). The third part of the plot demonstrates that chemically-derived farnesene can be hydrogenated at 100° C. with little or no catalyst deactivation.

In certain embodiments, the hydrogenation reaction occurs in a slurry reactor. In certain embodiments, the hydrogenation reaction occurs in a fixed bed reactor. In certain embodiments, the hydrogenation reaction occurs in a fluidized bed reactor. In certain embodiments, the hydrogenation reaction occurs in a batch reactor. In further embodiments, the hydrogenation reaction occurs in a continuous flow reactor.

Hydrogen for use in the process can be obtained from any source deemed suitable by one of skill in the art. Exemplary sources include Linde Group, Air Products Praxair, and Air Liquid. Alternatively, hydrogen can be generated by steam methane reforming where pressurized natural gas and deionized water are fed to a steam methane reformer and converted to hydrogen via the following overall reaction:

$$CH_4 \text{ (gas)} + 2H_2O \text{ (gas)} \rightarrow CO_2 \text{ (gas)} + 4 H_2 \text{ (gas)}.$$

Carbon monoxide, carbon dioxide, water, and other gaseous contaminants can be separated from hydrogen via pressure-swing adsorption. The resulting hydrogen purity is typically 99% or greater. Another method for in situ hydrogen generation is by electrolysis. De-mineralized water is fed to an electrolysis unit and is converted to hydrogen via the following reaction:

$$2H_2O \text{ (liquid)} \rightarrow O_2 \text{ (gas)} + 2 H_2 \text{ (gas)}.$$

In certain embodiments, the hydrogen composition used in the process is at least about 85%, 90%, 95%, 97%, 99% 99.5% or 99.99% pure. In certain embodiments, residual $CO_x$ is ≤50 ppm. In certain embodiments, the hydrogen composition includes no measurable $H_2S$.

Any hydrogenation catalyst can be used in the practice of a process provided herein. Exemplary catalysts are described, for example, in U.S. Pat. Nos. 6,403,844; 5,379, 767; 5,151,172; 4,968,612; and 3,702,348. In certain embodiments, the catalyst is selected from Ni, Pd, Ru, Pt, Rh, Ir, Cu and Fe; alloys of the platinum group catalysts with promoters or stabilizers such as Mo, Co, Mg, and Zn; Raney-type porous catalysts, such as Ni/Al, Co/Al, and Cu/Al; and hydroprocessing catalysts, such as NiMoS and CoMoS.

The catalyst can be provided in any suitable form, with a minimum dimension of, for example, at least 1 mm. Specific particle dimensions can be selected based upon reaction conditions and the type of catalyst bed being used. The catalyst can include any shape providing sufficient surface area, including but not limited to, cylinders, tablets, granules, spheres, lobed cylinders, or combinations thereof. The catalyst can also contain holes or passages. The particles can be formed by methods known in the art, such as, for example, extrusion or tabletting, or the like.

Although many catalysts can be used, an important factor for large scale hydrogenation is catalyst cost. In these situations, a catalyst is selected by balancing reactivity with costs. Of the platinum group metals, the order of reactivity was found to be Pd>Rh>Pt>>Ru. Fortuitously, the palladium catalysts also happen to be the least expensive of the highly active platinum group metals. For example, recent prices were: Pd=$200/oz; Rh=$1000/oz; Pt=$970/oz; Ru=$80/oz.

Figure 6:
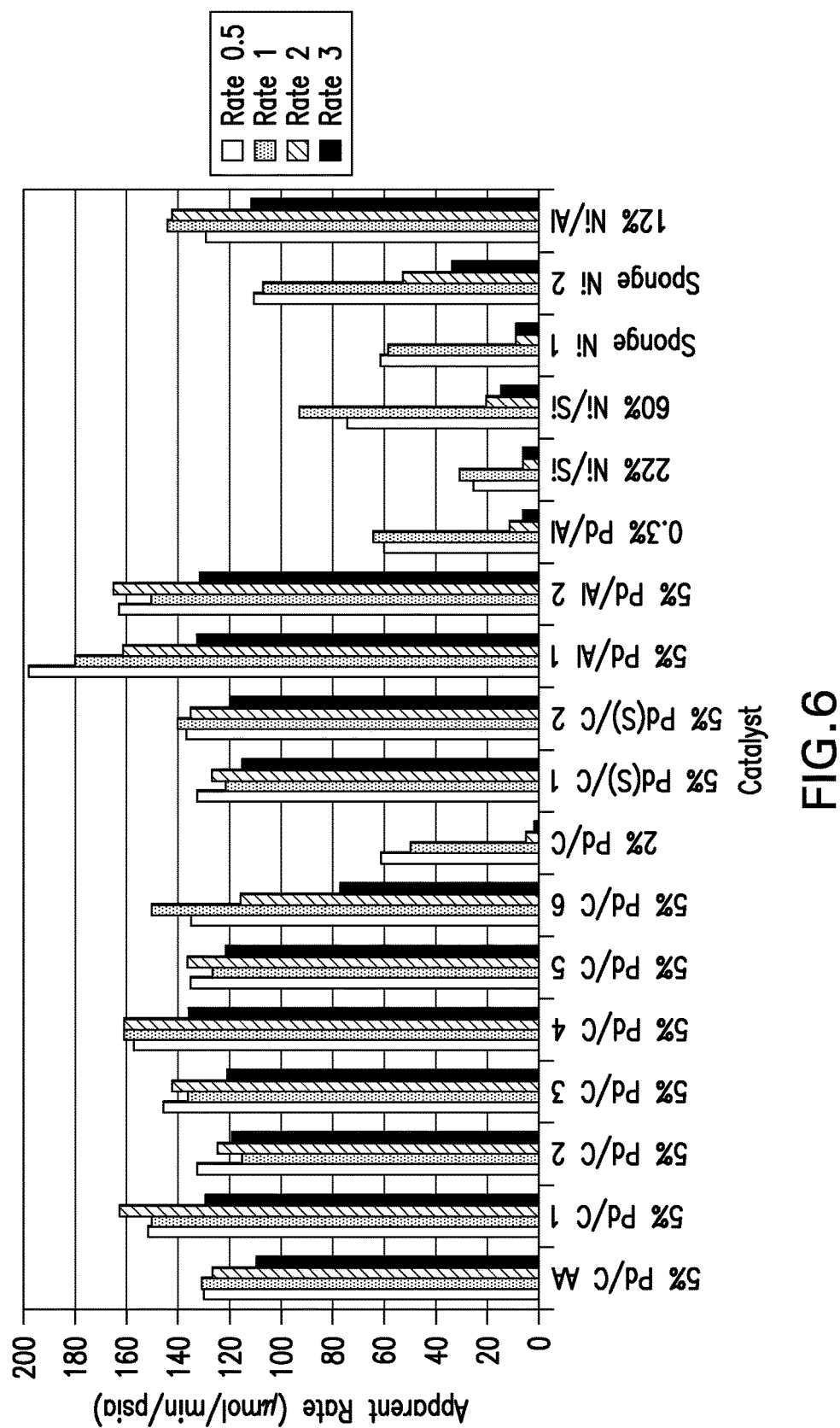
FIG. 6 is a plot of apparent hydrogenation rates for farnesene at 0.5, 1, 2, and 3 equivalents of hydrogen at 100° C. and 50 mg of catalyst loading.

Although good results have been achieved with Pd catalysts, particularly the 5% Pd/C catalyst, Pd catalyst costs still can be a significant expense on a commercial scale. As a result, various lower cost catalysts were screened. Various Pd and Ni catalysts as well as NiMo and CoMo hydroprocessing catalysts can be used. Based on these screens, the most cost effective catalysts were selected that performed well under low temperature and low catalyst loading conditions. An illustrative panel of catalysts and results are shown by FIG. 6 which shows the hydrogenation rate of limonene at 0.5, 1, 2, and 3 equivalents of hydrogen at 100° C. and 50 mg of catalyst loading.

Of these, Ni-based catalysts were identified as a very cost effective option while being capable of operating at extremely high LHSVs (Liquid Hourly Space Velocity). A recent price for Ni which is typically priced by the pound was $0.33/oz. Exemplary Ni catalysts include "Raney Ni", "sponge Ni", and "skeletal Ni". In certain embodiments, the catalyst is selected from Ni and Pd catalyst.

When the catalyst is used with a fixed bed support, any suitable material with high mechanical strength, high thermal stability, and low surface tension with supported metals can be used. In certain embodiments, useful support materials include, for example, silica, titania, zirconia, alumina, keiselguhr, magnesia, calcium aluminate cements, other inorganic carriers, carbon, and other known materials or modified versions of these supports such as base-treated versions, or versions with stabilizing additives such as MgO or oxides from the Lanthanide series. A catalyst support can be in the form of a pellet or extrudate with size dimensions on the order of 0.1-5 mm, 0.5-5 mm, 1-5 mm, 1-4, or 1-3 mm.

Exemplary Ni catalysts with a fixed bed support include $Al_2O_3$ supported Ni, Si-supported Ni, and sponge-type Ni. The activity of these catalysts can be optionally further modulated by the addition of a promoter or stabilizer such as Mo. Preferred Ni-based catalysts include $Al_2O_3$ supported catalysts such as 20%, 12%, or 8% $Ni/Al_2O_3$. These Ni-based catalysts also have a price advantage: although both 20% $Ni/Al_2O_3$ and 0.3% $Pd/Al_2O_3$ catalysts can provide similar hydrogenation performance, the cost per unit reactor volume of the 20% $Ni/Al_2O_3$ catalyst is approximately 40% of the cost of the 0.3% $Pd/Al_2O_3$ catalyst. In certain embodiments, the catalyst for use in a process provided herein is selected from 20% $Ni/Al_2O_3$ and 0.3% $Pd/Al_2O_3$.

When the hydrogenation reaction occurs in a fixed bed reactor, any suitable fixed bed reactor can be used. Exemplary reactors include a one-stage fixed bed reactor, a two-stage fixed bed reactor, and a multi-stage fixed bed reactor.

Many configurations of a fixed bed reactor are known in the art. Exemplary configurations include: i) cocurrent gas-liquid downflow where reactant liquid and hydrogen gas is fed to a fixed bed reactor cocurrently to the top, described, for instance, by R. Gupta, in "Cocurrent Gas-Liquid Downflow in Packed Beds", Chapter 19, of the *Handbook of Fluids in Motion* (1983); ii) cocurrent upflow where reactant liquid and hydrogen gas are fed to a fixed-bed reactor cocurrently to the bottom, and iii) countercurrent operations where reactant liquid and hydrogen gas are fed to a fixed-bed reactor countercurrently with liquid fed to the top trickling through rising hydrogen that is fed to the bottom, as described by P. Trambouze, in "Countercurrent Two-Phase Flow Fixed Bed Catalytic Reactions," *Chemical Engineering Science*, Vol 45, No. 8, pp 2269-2275 (1990).

The hydrogenation reactions described herein can be extremely exothermic, particularly when the immiscible olefin has multiple double bonds. As a consequence, strategies for removing potentially large amounts of heat need to be in place. For example, the hydrogenation of farnesene would result in a temperature rise of about 1000° C. if performed adiabatically. Thus, if hydrogenation were to occur in a slurry reactor or an ebullated bed reactor, heat would need to be continually removed. Because these systems are well-mixed, the heat of reaction can be transferred to internal cooling coils or external cooling jackets efficiently. Because of the complexities in having mechanical agitation, the limitation in size imposed thereof, as well as the requirement for catalyst filtration, mechanically-agitated slurry reactors may be more useful for smaller scale reactions.

In certain embodiments, fixed bed reactors are used for large scale hydrogenations. These reactors have the advantage of simplicity because they require no mechanical agitation or catalyst filtration.

Various strategies can be used to remove heat from fixed bed reactors. In certain embodiments, a plurality of small diameter reaction tubes can be used. The small diameter can allow heat of reaction to be conducted radially out of the tubes effectively due to the short distance the heat needs to conduct over.

Figure 8:
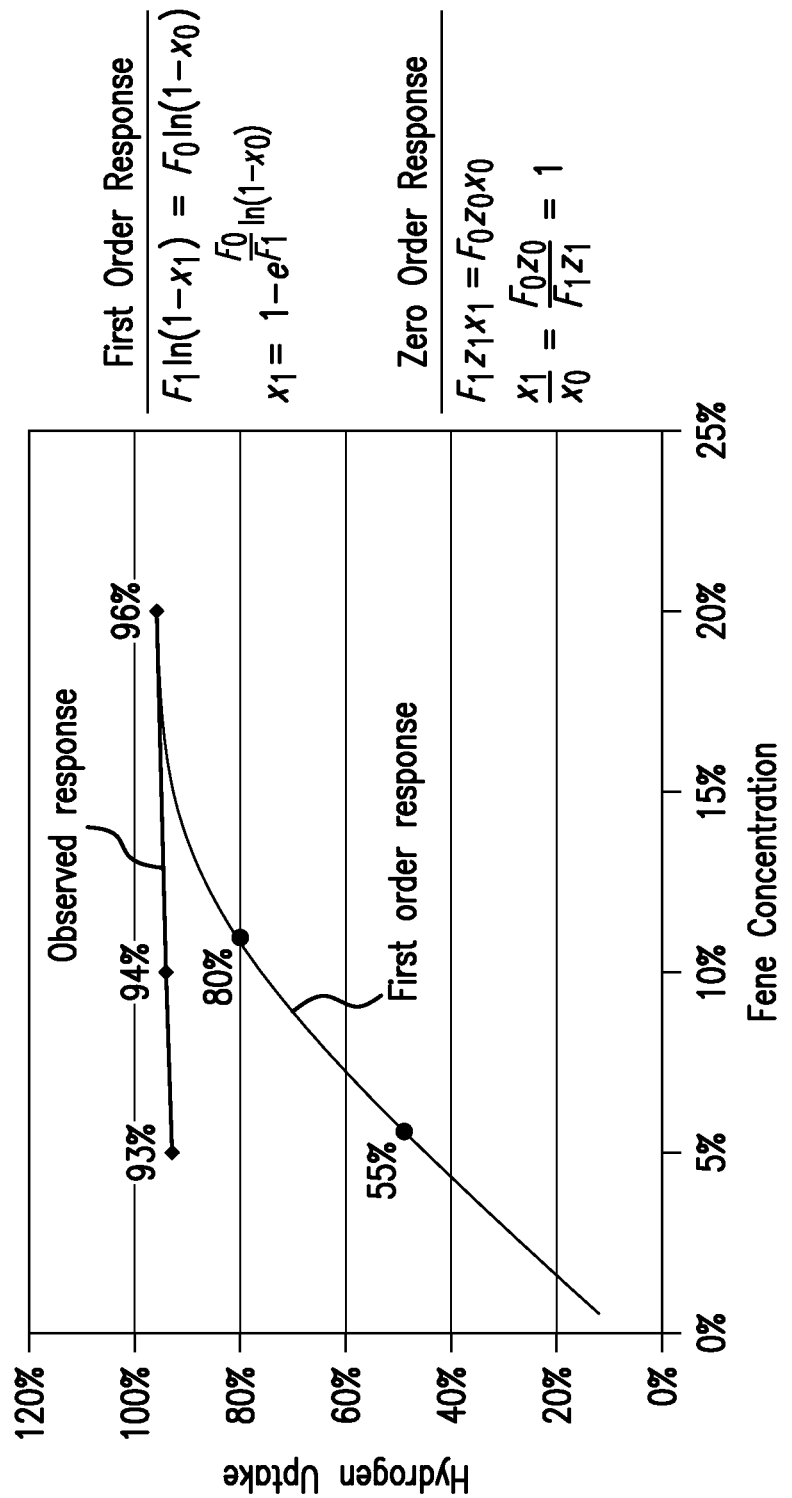
FIG. 8 is a plot of hydrogenation uptake rate for farnesene versus farnesene concentration showing that hydrogenation of farnesene displays zero-order kinetics and no substrate mass transfer resistance.

In certain embodiments, a chilled product stream can be recycled from the reactor effluent to act as a diluent. In one embodiment, the diluent is the intended product, a saturated immiscible olefin. The cold effluent can act as a heat sink for the heat of reaction so that the temperature rise for a fixed rate of reactant addition decreases as more product liquid is mixed into the feed. This strategy is particularly effective when the hydrogenation of the reactant exhibits zero order kinetics. For example, FIG. 8 is a plot of the hydrogen uptake versus various dilution of farnesene. A calculated curve for a first order reaction based on hydrogen uptake of 20% farnescene concentration is shown along with the observed response for farnesene. As it can be seen, because a reactant like farnesene exhibits zero order kinetics, dilute solutions (less than <20%, <15%, <10%, and even <5%) can be efficiently hydrogenated.

In other embodiments, the diluent is a compound or composition that is inert under the employed hydrogenation conditions. Illustrative examples include saturated hydrocarbons that are not the hydrogenated immiscible olefin. For example, diluents can be n-pentane, n-hexane, n-heptane, n-octane, n-decane, and the like.

In still other embodiments, the diluent is a hydrogenated immiscible olefin. In certain embodiments, the diluent is a saturated immiscible olefin.

In another aspect, a hydrogenation method using a fixed bed reactor is provided. The method comprises:
  a) providing a feed stream to the inlet of a fixed bed reactor wherein the feed stream comprises an immiscible olefin and a diluent composition;
  b) contacting the feed stream with hydrogen in the presence of a hydrogenation catalyst at a temperature greater than room temperature thereby producing an effluent;
  c) separating the effluent which comprises a hydrogenated immiscible olefin into a product stream comprising a hydrogenated immiscible olefin and a recycle stream comprising a hydrogenated immiscible olefin;
  d) adding the recycle stream as part of the diluent composition to a stream comprising the immiscible olefin to form a feed stream comprising recycled hydrogenated immiscible olefin;
  e) providing the feed stream comprising recycled hydrogenated immiscible olefin to the inlet of the fixed bed reactor; and
  f) repeating steps b)-e) at least once.

In another aspect, a hydrogenation method comprises:
  a) providing a feed stream to the inlet of a fixed bed reactor wherein the feed stream comprises an immiscible olefin and a diluent composition;
  b) contacting the feed stream with hydrogen in the presence of a hydrogenation catalyst at a temperature greater than about 100° C. thereby producing an effluent;
  c) separating the effluent which comprises a hydrogenated immiscible olefin into a product stream comprising a hydrogenated immiscible olefin and a recycle stream comprising a hydrogenated immiscible olefin;
  d) adding the recycle stream as part of the diluent composition to a stream comprising the immiscible olefin to form a feed stream comprising recycled hydrogenated immiscible olefin;
  e) providing the feed stream comprising recycled hydrogenated immiscible olefin to the inlet of the fixed bed reactor; and
  f) repeating steps b)-e) at least once.

In certain embodiments, the immiscible olefin is part of a crude olefin composition. In certain embodiments, the immiscible olefin is part of a purified olefin composition.

In certain embodiments, the diluent composition comprises a hydrogenated immiscible olefin. In certain embodiments, the diluent composition comprises a saturated immiscible olefin. In certain embodiments, the diluent composition comprises recycled hydrogenated immiscible olefin in combination with one or more other diluents. In further embodiments, the diluent composition comprises recycled saturated immiscible olefin in combination with one or more other diluents.

In certain embodiments, the feed stream comprises about 1%, 5%, 10%, 25%, 50%, 75%, 90%, 95%, 99% or less diluent based on total weight of the immiscible olefin. In certain embodiments, the feed stream comprises about 50 to 95%, 30 to 95%, 20 to 95%, or 5 to 99% diluent based on total weight of the immiscible olefin. In certain embodiments, the feed stream comprises about 99%, 95%, 90%, 85%, 75%, 65%, 55%, 45%, 35%, 25%, 15%, 5% or 1% diluent based on total weight of the immiscible olefin.

In certain embodiments, the feed stream comprises about 1%, 5%, 10%, 25%, 50%, 75%, 90%, 95%, 99% or less hydrogenated immiscible olefin based on total weight of the diluent. In further embodiments, the feed stream comprises about 50 to 95%, 50 to 90%, 30 to 95%, 20 to 95%, 5 to 97% or 60 to 85% hydrogenated immiscible olefin based on total weight of the diluent. In certain embodiments, the feed stream comprises about 99%, 95%, 90%, 85%, 75%, 65%, 55%, 45%, 35%, 25%, 15%, 5% or 1% hydrogenated immiscible olefin based on total weight of the diluent. In additional embodiments, the feed stream comprises about 50 to 95%, 50 to 90%, 30 to 95%, 20 to 95%, 5 to 97% or 60 to 85% saturated immiscible olefin based on total weight of the diluent. In further embodiments, the feed stream comprises about 99%, 95%, 90%, 85%, 75%, 65%, 55%, 45%, 35%, 25%, 15%, 5% or 1% saturated immiscible olefin based on total weight of the diluent.

In certain embodiments, the feed stream comprises about 5%, 10%, 25%, 50%, or 75% or less immiscible olefin based on total weight of the feed stream. In further embodiments, the feed stream comprises about 1 to 50%, 5 to 50%, 5 to 25%, 10 to 50%, 10 to 40% or 10 to 25% immiscible olefin based on total weight of the feed stream. In certain embodiments, the feed stream comprises about 50%, 40%, 30%, 25%, 20%, 10%, 5% or 1% immiscible olefin based on total weight of the feed stream.

In certain embodiments, the catalyst is a Pd catalyst. In certain embodiments the catalyst is a Ni catalyst. In certain embodiments, the catalyst is $Ni/Al_2O_3$.

In certain embodiments, the temperature difference between the inlet and the outlet of the fixed bed reactor is not more than 200° C. In certain embodiments, the temperature difference between the inlet and the outlet of the fixed bed reactor is not more than 100° C. In certain embodiments, the temperature difference between the inlet and the outlet of the fixed bed reactor is not more than 50° C.

Figure 9:
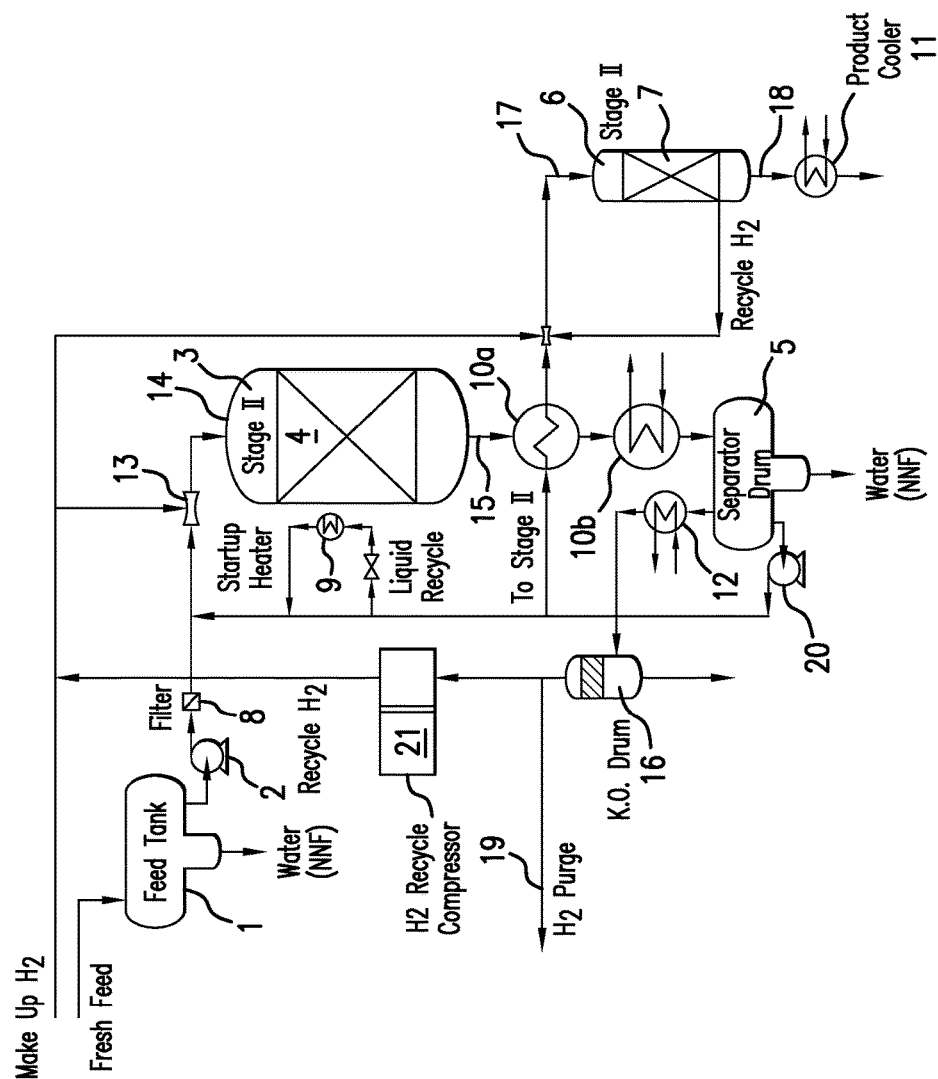
FIG. 9 is a schematic of an exemplary hydrogenation system for the practice of an embodiment of the hydrogenation process provided herein.

FIG. 9 is a schematic of an exemplary fixed bed hydrogenation system. The system comprises a primary reactor 3

(with primary catalyst 4). Optionally, the system comprises a secondary reactor 6 (with secondary catalyst 7). The primary catalyst and the secondary catalyst may be identical or they may be different. If the system comprises only a primary reactor, this is a one-stage reactor where hydrogenation occurs in the primary reactor and the hydrogenated immiscible olefin is separated into two fractions: a recycling fraction and a product fraction. The recycling fraction is then recirculated as a diluent for the immiscible olefin feed. The hydrogenated immiscible olefin that is the product fraction can be used without further treatment.

If the system comprises both a primary and secondary reactor, this is a two-stage reactor. As with the one-stage reactor, hydrogenation occurs in the primary reactor and the hydrogenated immiscible olefin is separated into two fractions: a recycling fraction and a product fraction. The recycling fraction is then recirculated as a diluent for the immiscible olefin feed to the primary reactor. The hydrogenated immiscible olefin that is the product fraction can be further hydrogenated to remove any residual unsaturation.

In addition to the reactors 3 and 6 depicted in FIG. 9, the system can comprise a feed holding tank 1, a liquid pump 2, a separator drum 5 to separate gas from liquid, and hydrogen recycle compressor 21. The system can include one or more of the following: a filter for immiscible olefin feed 8, a startup heater to heat the feed 9 to a desired temperature, an interchanger 10a and a cooler 10b for the product exiting from the primary reactor, a cooler 11 for the product exiting from the secondary reactor, a cooler 12 for hydrogen exiting the separator drum, a tee or Venturi-type eductor 13 where the immiscible olefin feed is mixed with hydrogen, a primary reactor inlet 14, a primary reactor outlet 15, a knockout pot 16 to separate gas and vapour, a secondary reactor inlet 17, a secondary reactor outlet 18, a vent 19 to purge gases from the system and a liquid pump 20.

In some embodiments where a fixed bed reactor is used, the immiscible olefin is mixed with a diluent. In certain embodiments, immiscible olefin feed entering the reactor comprises between about 5% and 20% immiscible olefin by volume. In certain embodiments, immiscible olefin feed entering the reactor is between about 5%, 10%, 15% and 20% immiscible olefin by volume.

In certain embodiments, the diluted immiscible olefin feed is mixed with hydrogen in a tee or Venturi-type eductor 13. In certain embodiments, about 1-1000%, 10-500 or 50-100% stoichiometric excess hydrogen, or about 100-5000, 100-2000, 200-1000 or 200-400 standard cubic feet per barrel of feed (scf/bbl) is used in the process. In certain embodiments, about 100% stoichiometric excess hydrogen, or about 200 standard cubic feed per barrel of feed (scf/bbl) is used in the process.

In certain embodiments, the hydrogenation process is carried out at pressures between about 100 psig to about 700 psig. The pressure typically is between 100 and 700 psig at reaction inlet 14 and between 5 and 10000 psig at reaction outlet 15. In certain embodiments, pressure at reaction inlet 14 is about 400 psig, 450 psig, 500 psig, 530 psig or 550 psig. In one embodiment, pressure at reaction inlet 14 is about 530 psig. In one embodiment, pressure at reaction outlet 15 is about 400 psig, 450 psig, 500 psig, or 550 psig. In one embodiment, pressure at reaction inlet 14 is about 530 psig and pressure at outlet 15 is about 500 psig.

In certain embodiments, the temperature during the process depends upon the operating pressures but typically a hydrogenation process is carried out at temperature greater than 100° C. In certain embodiments, the temperature is about 110 to 200° C. at the inlet 14 and between about 150 to 350° C. at the outlet 15.

In certain embodiments, an axial temperature rise is specified based on the difference between the reaction light-off temperature and the temperature at which the catalyst begins to foul. In other embodiments, in the hydrogenation process is near, but above the temperature at which the hydrogenation of begins, i.e., light-off temperature, and below the temperature at which catalyst fouling or lost product yield are significant. In certain embodiments, the axial temperature rise in the process is in the range of 10 to 300° C. In certain embodiments, the axial temperature rise in the process is about 10, 20, 30, 40, 45, 50, 55, 60, 65, 70, 80, 100, 150, 200 or 300° C. Exemplary hydrogenation reactions with axial temperature rise at about 200° C. are described in U.S. Pat. No. 3,796,764.

In certain embodiments, the temperature at the inlet 14 of the reactor is about 150° C., and the pressure is about 530 psig. In one embodiment, the multi-phase feed flow and hydrogen stream are forced down the reactor 3 by the dynamic pressure drop, and exits the reactor at about 500 psig.

In certain embodiments, primary reactor 3 comprises a sacrificial layer of catalyst or an adsorbent at the head of the reactor, to accumulate any irreversibly binding catalyst poisons and prevent them from accumulating on the catalyst below. In certain embodiments, the sacrificial layer is composed of a support having a larger particle size, larger pore dimensions, and/or lower metal loading than the catalyst. In certain embodiments, larger particle and pore dimensions of the sacrificial layer support allow more material to accumulate on the sacrificial section before the pores and interstitial spaces become clogged, which results in large pressure drop necessary to drive flow. In further embodiments, a lower metal content of the sacrificial layer can reduce catalyst cost and can decrease hydrogenation rate at active sites, which can increase hydrogen availability at active sites and can decrease the potential for side reactions, including catalyst coking reactions that may occur in the absence of hydrogen. In still further embodiments, one, two, three or multiple sacrificial layers are present in the fixed bed. In additional embodiments, the sacrificial layer of catalyst comprises a topmost layer of a catalyst support material, such as $Al_2O_3$, followed by a layer of a low loading of Ni on a suitable support, such as $Al_2O_3$, in order to prolong the life of the sacrificial layers.

Primary reactor 3 can further comprise a primary catalyst 4. In one embodiment, the primary catalyst is a Ni catalyst containing about 20% Ni supported on alumina extrudate, with an extrudate diameter of 1-5 mm. An example of a catalyst for use in the process is HTC NI 500 RP 1.2 mm available from Johnson-Matthey. In certain embodiments, the Ni loading in the catalyst is about 10%, 7%, 5%, 3% or less. In one embodiment, the Ni loading in the catalyst is about 5% or less. In certain embodiments, the loading of Ni is about 60% or greater to minimize reactor volume and/or prolong catalyst life. In certain embodiments, the primary catalyst comprises 0.3% $Pd/Al_2O_3$.

In certain embodiments, primary reactor 3 is sized with a reactor LHSV (Liquid Hourly Space Velocity) of 2, 5, 10, 15, 20 or 25, meaning that the ratio of the volumetric feed of liquid per hour to the volume of the primary catalyst bed is 2, 5, 10, 15, 20 or 25. In certain embodiments, the primary reactor is sized with a reactor LHSV of 20. If the immiscible olefin is diluted such that the feed is about 5% olefin and 95% hydrogenated product, this is equivalent to a process LHSV of 1, meaning that the ratio of the volumetric feed of immiscible olefin per hour to the volume of the primary catalyst bed is 1. In certain embodiments, the process is operated at LHSV of 2 or higher.

In certain embodiments, the aspect ratio (ratio of reactor height:diameter) for reactor 3 is between about 0.5 to 100, 0.5 to 50, 0.5 to 30, 0.5 to 20, 1 to 15, 1 to 10, 1 to 7 or about 1 to 5. In certain embodiments, the aspect ratio is between 1 and 5. In general, lower aspect ratios decrease the pressure drop across the reactor, and therefore the electrical consumption of the recycle pump and recycle compressor. Higher aspect ratios can result in greater turbulent mixing of the reacting fluids, which improves mass and heat transfer, which may mitigate the potential for catalyst fouling and hot spot formation.

In certain embodiments, the primary reactor contains a fluid distributor at the top of the reactor, for example, to evenly distribute the multi-phase reactant flow across the width of the reactor. In certain embodiment, one or more additional fluid distributors are positioned further into the reactor. In certain embodiments, one or more additional fluid distributors are positioned such that the fluid in the reactor is re-distributed once every 30 feet of catalyst height.

In certain embodiments, product exiting at the bottom of the reactor is cooled by an interchanger 10a and a cooler 10b. In certain embodiments, the product exits at the bottom of the reactor at about 195° C. and about 500 psig. The excess hydrogen (e.g., ~100 scf $H_2$/bbl liquid) can be disengaged from the liquid reactants in the gas/liquid separator 5. Excess hydrogen can be pulled through a gas cooler 12 and a knock-out pot 16 by a recycle compressor 21. A purge stream can release between ~1% and ~10% of the recycled hydrogen to vent 19. This can allow small amounts of gases generated during the reaction, such as methane, to exit the system. The recycled hydrogen can be mixed with make-up hydrogen downstream of the compressor 21, before mixing with the immiscible olefin feed.

In certain embodiments, a fraction of the cooled liquid product from primary reactor 3 is recycled by a liquid pump 20 to the head of reactor 3 as a recycle product fraction to dilute incoming, fresh immiscible olefin feed. A remaining fraction of the liquid product can be diverted to a second reaction stage for polishing, which can reduce the residual unsaturation in the product fraction to the desired specification of the final hydrogenation product. A stoichiometric amount of hydrogen can be added to the second stage.

The secondary reactor 6 contains a secondary catalyst 7. In certain embodiments, the secondary catalyst has a similar catalyst loading as the primary catalyst 4, or it may be loaded with a higher-activity catalyst, such as a high loading of supported Pd. In certain embodiments, the secondary reactor 6 comprises 5% $Pd/Al_2O_3$ catalyst. In certain embodiments, the secondary reactor is sized with a reactor LHSV of 1, 2, 3, 4, 5 or 7. In certain embodiments, the secondary reactor is sized so that its LHSV is 5.

In certain embodiments, the secondary reactor operates at about 300 to 500 psig. In certain embodiments, the secondary reactor operates at about 130-200° C. In certain embodiments, the secondary reactor operates at about 500 psig and at about 150-190° C.

In another aspect, a hydrogenation method using existing hydroprocessing equipment is provided. Because hydroprocessing typically occurs in a refinery setting, they are able to handle high temperature reactions. In this method, hydrogenation of the immiscible olefin and hydroprocessing of the unfinished diesel occurs in the same reactor resulting in a saturated olefin and a finished diesel that has a reduced sulfur content that is 50 ppmw or less. The method comprises:

a) providing a feed stream to the inlet of a fixed bed reactor wherein the feed stream comprises an immiscible olefin and a diluent composition; and b) contacting the feed stream with hydrogen in the presence of a hydrogenation catalyst at a temperature greater than about 100° C. thereby producing an effluent, wherein the diluent composition is an unfinished diesel that has a sulfur content greater than 50 ppmw and the effluent comprises saturated immiscible olefin and the effluent has a sulfur content that is less than 50 ppmw.

In certain embodiments, the immiscible olefin is part of a crude olefin composition. In certain embodiments, the immiscible olefin is part of a purified olefin composition.

In certain embodiments, the unfinished diesel has a sulfur content that is greater than 100 ppmw, greater than 500 ppmw, greater than 1000 ppmw, greater than 5000 ppmw, or greater than 10,000 ppmw. In other embodiments the unfinished diesel has a nitrogen content that is greater than 10 ppmw, greater than 50 ppmw, greater than 100 ppmw, greater than 500 ppmw, greater than 1000 ppmw, greater than 5000 ppmw, or greater than 10,000 ppmw.

In certain embodiments, the effluent or the finished diesel has a sulfur content that is less than 30 ppmw. In other embodiments, the effluent has a sulfur content that is less than 15 ppmw. In still other embodiments, the effluent has a nitrogen content that is less than 1 ppmw.

Alternatively, the unfinished diesel could be used as a diluent as described above. In this method, hydrogenation of the immiscible olefin and hydroprocessing of the unfinished diesel occurs in the same reactor but the effluent is recycled to control the temperature of the reaction. The method comprises:

a) providing a feed stream to the inlet of a fixed bed reactor wherein the feed stream comprises an immiscible olefin and a diluent composition wherein the diluent composition comprises unfinished diesel that has a sulfur content that is greater than 50 ppmw such that the feed stream has a sulfur content that is greater than 50 ppmw;

b) contacting the feed stream with hydrogen in the presence of a hydrogenation catalyst at a temperature greater than about 100° C. thereby producing an effluent wherein the effluent comprises saturated immiscible olefin and the effluent has a sulfur content that is less than 50 ppmw;

c) diverting part of the effluent stream into a recycle stream comprising a finished diesel that has a sulfur content that is less than 50 ppmw;

d) adding the recycle stream as part of the diluent composition to a stream comprising the immiscible olefin to form a feed stream comprising immiscible olefin and the feed stream has a sulfur content that is greater than 50 ppmw;

e) providing the feed stream to the inlet of the fixed bed reactor; and f) repeating steps b)-e) at least once.

In certain embodiments, the immiscible olefin is part of a crude olefin composition. In certain embodiments, the immiscible olefin is part of a purified olefin composition.

In certain embodiments, the unfinished diesel has a sulfur content that is greater than 100 ppmw, greater than 500 ppmw, greater than 1000 ppmw, greater than 5000 ppmw, or greater than 10,000 ppmw. In other embodiments the unfinished diesel has a nitrogen content that is greater than 10 ppmw, greater than 50 ppmw, greater than 100 ppmw, greater than 500 ppmw, greater than 1000 ppmw, greater than 5000 ppmw, or greater than 10,000 ppmw.

In certain embodiments, the effluent has a sulfur content that is less than 30 ppmw. In other embodiments, the effluent has a sulfur content that is less than 15 ppmw. In still other embodiments, the effluent has a nitrogen content that is less than 1 ppmw.

In certain embodiments, the feed stream comprises about 1%, 5%, 10%, 25%, 50%, 75%, 90%, 95%, 99% or less diluent based on total weight of the immiscible olefin. In certain embodiments, the feed stream comprises about 50 to 95%, 30 to 95%, 20 to 95%, or 5 to 99% diluent based on total weight of the immiscible olefin. In certain embodiments, the feed stream comprises about 99%, 95%, 90%, 85%, 75%, 65%, 55%, 45%, 35%, 25%, 15%, 5% or 1% diluent based on total weight of the immiscible olefin.

In certain embodiments, the diluent composition comprises unfinished diesel that has a sulfur content that is greater than 50 ppmw and a hydrogenated immiscible olefin. In certain embodiments, the feed stream comprises about 1%, 5%, 10%, 25%, 50%, 75%, 90%, 95%, 99% or less unfinished diesel based on total weight of the diluent. In certain embodiments, the diluent composition comprises about 99%, 95%, 90%, 85%, 75%, 65%, 55%, 45%, 35%, 25%, 15%, 5% or 1% unfinished diesel based on total weight of the diluent.

In certain embodiments, the feed stream comprises about 1%, 5%, 10%, 25%, 50%, 75%, 90%, 95%, 99% or less hydrogenated immiscible olefin based on total weight of the diluent. In further embodiments, the feed stream comprises about 50 to 95%, 50 to 90%, 30 to 95%, 20 to 95%, 5 to 97% or 60 to 85% hydrogenated immiscible olefin based on total weight of the diluent. In certain embodiments, the feed stream comprises about 99%, 95%, 90%, 85%, 75%, 65%, 55%, 45%, 35%, 25%, 15%, 5% or 1% hydrogenated immiscible olefin based on total weight of the diluent. In additional embodiments, the feed stream comprises about 50 to 95%, 50 to 90%, 30 to 95%, 20 to 95%, 5 to 97% or 60 to 85% saturated immiscible olefin based on total weight of the diluent. In further embodiments, the feed stream comprises about 99%, 95%, 90%, 85%, 75%, 65%, 55%, 45%, 35%, 25%, 15%, 5% or 1% saturated immiscible olefin based on total weight of the diluent.

In certain embodiments, the feed stream comprises about 5%, 10%, 25%, 50%, or 75% or less immiscible olefin based on total weight of the feed stream. In further embodiments, the feed stream comprises about 1 to 50%, 5 to 50%, 5 to 25%, 10 to 50%, 10 to 40% or 10 to 25% immiscible olefin based on total weight of the feed stream. In certain embodiments, the feed stream comprises about 50%, 40%, 30%, 25%, 20%, 10%, 5% or 1% immiscible olefin based on total weight of the feed stream.

In certain embodiments, the catalyst is a hydroprocessing catalyst. In certain embodiments the catalyst is a Ni catalyst. In certain embodiments, the catalyst is NiMo catalyst.

Farnesene

In another aspect, a purified farnesene composition is provided. The composition comprises:

a microbial-derived mixture comprising farnesene in an amount that is equal to or greater than about 93% by weight and the following compounds each of which is present in an amount that is equal to or greater than about 0.1% by weight: bisabolene, zingiberene, farnesol, and farnesene epoxide; and, a phenolic antioxidant wherein the phenolic antioxidant is present an amount that is at least about 0.0001% by weight.

In another aspect, a purified farnesene composition is provided. The composition comprises:

a microbial-derived mixture comprising farnesene in an amount that is equal to or greater than about 93% by weight and the following compounds each of which is present in an amount that is equal to or greater than about 0.1% by weight: bisabolene, zingiberene, farnesol, and farnesene epoxide; and, a phenolic antioxidant wherein the phenolic antioxidant is present an amount that is at least about 0.001% by weight.

In certain embodiments, the phenolic antioxidant is present in an amount that is at least about 0.0005% by weight. In certain embodiments, the phenolic antioxidant is present in an amount that is at least about 0.005% by weight. In certain embodiments, the phenolic antioxidant is present in an amount that is between about 0.005% and about 0.5% by weight. In further embodiments, the phenolic antioxidant is present in an amount that is at least about 0.01% by weight. In additional embodiments, the phenolic antioxidant is present in an amount that is between about 0.05% and about 0.3% by weight. In certain embodiments, the phenolic antioxidant is present in an amount that is greater than about 0.5% by weight.

In certain embodiments, the microbial-derived mixture further comprises squalene. The amount of squalene is generally less than about 0.5% based on total weight of the microbial-derived farnesene. In certain embodiments, the amount of squalene is about 0.05% to 0.5% based on total weight of the microbial-derived farnesene. In further embodiments, the amount of squalene is about 0.05%, 0.08%, 0.09%, or 0.1% based on total weight of the microbial-derived farnesene.

In some cases, the microbial-derived mixture further comprises farnesene dimers, such 1,4 and 1,3 adducts of farnesene. The amount of dimers is typically less than about 0.5% based on total weight of the microbial-derived farnesane. In certain embodiments, the amount of farnesene dimers is about 0.05%, 0.07%, 0.09%, 0.1%, 0.15%, 0.2%, 0.25%, 0.3% or 0.5% based on total weight of the microbial-derived farnesene. In certain embodiments, the amount of farnesene dimers is about 0.2% based on total weight of the microbial-derived farnesene.

When the microbial-derived farnesene composition is hydrogenated, farnesene hydrogenates to farnesane. Both bisabolene and zingiberene hydrogenate to bisabolane. Farnesol becomes either farnesane (eliminates the hydroxyl group to form farnesene which then subsequently hydrogenates to become farnesane) or forms 2,6,10-trimethylundecane (plus methane and water). The latter reaction is depicted below:

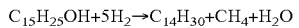

Farnesene epoxide is hydrogenated to farnesol which is converted into farnesane or 2,6,10-trimethylundecane as depicted above.

Thus in another aspect, a purified farnesane composition is provided. The composition comprises: farnesane in an amount that is equal to or greater than about 93% by weight and bisabolane in an amount that is equal to or greater than about 0.1% by weight, wherein the wt. % is based on the total weight of farnesane. In some embodiments, the amount of bisabolane is equal to or greater than about 0.2%, 0.3%, 0.4%, 0.5%, 0.6%, 0.7%, 0.8%, 0.9% or 1.0% based on the total weight of farnesane. In other embodiments, the composition comprises: farnesane in an amount that is equal to or greater than about 93% by weight; bisabolane in an amount that is equal to or greater than about 0.1% by weight; and 2,6,10-trimethylundecane in an amount that is equal to or greater than about 0.1% by weight.

In cases where the microbial-derived farnesene mixture includes squalene, then the purified composition will further comprise squalane. The amount of squalane is generally less than about 0.5% based on total weight of the farnesane. In certain embodiments, the amount of squalane is about 0.05% to 0.5% based on total weight of the farnesane. In further embodiments, the amount of squalane is about 0.05%, 0.08%, 0.09%, or 0.1% based on total weight of the farnesane.

In some cases where the microbial-derived farnesene mixture includes farnesene dimers, the purified farnesane composition further comprises farnesane dimers, the hydrogenated versions of farnesene dimers. The amount of dimers is typically less than about 0.5% based on total weight of the farnesane. In one embodiment, the amount of farnesene dimers is about 0.05%, 0.07%, 0.09%, 0.1%, 0.15%, 0.2%, 0.25%, 0.3% or 0.5% based on total weight of the farnesane. In one embodiment, the amount of farnesane dimers is about 0.2% based on total weight of the farnesane.

In certain embodiments, the product of hydrogenation of a microbial-derived farnesene mixture comprises unsaturated farnesane. In certain embodiments, the product comprises a monounsaturated farnesane. In certain embodiments, the product comprises farnesane and an unsaturated farnesane. In further embodiments, the product comprises about 0.1 to 50%, 0.1 to 25%, or 0.1 to 10% monounsaturated farnesane by total weight of the product. In still further embodiments, the product comprises about 0.1% monounsaturated farnesane. In additional embodiments, the product comprises about 10 to 99.9%, 20 to 99.9%, 50 to 99.9%, 50 to 99%, or 50 to 90% farnesane by total weight of the product. In still additional embodiments, the product comprises at least about 99.9% farnesane by total weight of the product.

In certain embodiments, a process provided herein comprises selective hydrogenation of farnesene to reduce one, two, three or four double bonds in farnesene. In one embodiment, a process yields a combination of hydrogenated farnesene products. In one embodiment, a product obtained in the hydrogenation process comprises a combination of farnesane and one or more monounsaturated farnesane products. In certain embodiments, a product comprises a monounsaturated farnesane in an amount from about 0.1 to 50% by total weight of the product. In certain embodiments, the amount of monounsaturated farnesane in a product is about 0.1, 1, 10, 25 or 50% by total weight of the product.

While the processes and systems provided herein have been described with respect to a limited number of embodiments, the specific features of one embodiment should not be attributed to other embodiments of the processes or systems. No single embodiment is representative of all aspects of the methods or systems. In certain embodiments, the processes may include numerous steps not mentioned herein. In certain embodiments, the processes do not include any steps not enumerated herein. Variations and modifications from the described embodiments exist.

It is noted that the processes for generation of hydrogenated microbial-olefins are described with reference to a number of steps. In certain embodiments, these steps can be practiced in any sequence. In certain embodiments, one or more steps may be omitted or combined but still achieve substantially the same results. The appended claims intend to cover all such variations and modifications as falling within the scope of the claimed subject matter.

All publications and patent applications mentioned in this specification are herein incorporated by reference to the same extent as if each individual publication or patent application was specifically and individually indicated to be incorporated by reference. Although the claimed subject matter has been described in some detail by way of illustration and example for purposes of clarity of understanding, it will be readily apparent to those of ordinary skill in the art in light of the teachings herein that certain changes and modifications may be made thereto without departing from the spirit or scope of the appended claims.

EXAMPLE

Example 1

This example describes the purification of farnesene that was produced by farnesene producing yeast strain A.

The yeast cells were separated from the fermentation broth using a continuous disk stack nozzle centrifuge (Alfa Laval DX 203 B-34). In addition to removing the cells, this step also served to concentrate the bio-organic compound in a smaller volume. For this particular yeast strain, a twenty fold concentration resulted in a composition that was approximately half farnesene and half fermentation medium. So for a twenty fold concentration, approximately 95% of the volumetric flow exited the centrifuge from the nozzles (cells+liquid) as waste while approximately 5% of the volumetric flow was captured as concentrated bio-organic composition.

This composition when allowed to settle or centrifuged, separated into three distinct phases. The top layer comprised primarily the immiscible olefin. The middle layer comprised emulsion formed by the cells, the immiscible olefin and water. The bottom layer comprised the aqueous fermentation medium.

The pH of the concentrated composition was adjusted to pH 8.3 using 5 N NaOH, followed by incubation at about 30° C. for approximately one hour. The concentrated composition (pH~8.3) was then subjected to liquid/liquid separation using the same centrifuge. Table 1 details the amounts of the bio-organic compound in each of the three phases (bio-organic compound layer; emulsion; and the aqueous layer) of the basic concentrated bio-organic composition.

TABLE 1

| liquid/liquid recovery of the concentrated composition at pH 8.3 | |
| --- | --- |
| Layer | % of farnesene |
| bio-organic | 82% (1.15 L) |
| Emulsion | 8% |
| Aqueous | 10% |

The farnesene purity was 94.9% (w/w). The total acid number as measured by ASTM D 664 was 0.9 mg KOH/g.

Example 2

This example describes further purification of farnesene from Example 1.

The farnesene was incubated with 0.4% w/w calcium hydroxide (e.g., Acros Organics, >98% pure, Cat. No. 21918000) for 2.5 hours at ambient temperature. This results in precipitation of various impurities which can be removed by various methods including centrifugation and filtration to yield a farnesene composition in which the organic acids that were extracted during the purification are neutralized. If desired, this neutralized composition can be further purified, for example, by distillation. Table 2 describes the total acid number and glycerin content of the various compositions.

TABLE 2

TAN & Glycerin content

| Analytical Test | | Crude | Ca(OH)$_2$ treated | Distilled |
|---|---|---|---|---|
| TAN (mg KOH/g of immiscible olefin) | | 0.5 | 0 | 0 |
| | Sterols | 0.31 | 0.315 | none detected |
| Glycerin % w | Free Glycerin | none detected | none detected | none detected |
| | Total Glycerin | 0.048 | 0.047 | 0.007 |
| | Monoglyceride | 0.086 | 0.087 | 0.027 |
| | Diglyceride | 0.017 | 0.014 | none detected |
| | Triglyceride | 0.213 | 0.205 | none detected |

TABLE 3

Hydrocarbon quantification

| Hydrocarbon | Crude (% area) | Ca(OH)2 treated (% area) | Distilled (% area) |
|---|---|---|---|
| Farnesene | 98.46 | 98.47 | 98.56 |
| Zingiberene | 0.286 | 0.285 | 0.287 |
| Bisabolene | 0.198 | 0.198 | 0.197 |
| Farnesene Epoxide | 0.193 | 0.194 | 0.193 |
| Bisabolol | 0 | 0.1 | 0 |
| Farnesol Isomer | 0.414 | 0.42 | 0.414 |
| Farnesol | 0.357 | 0.354 | 0.351 |
| Squalene | 0 | 0 | 0 |
| Farnesene Dimer | 0 | 0 | 0 |
| Ergosterol | 0 | 0 | 0 |

TABLE 4

Trace Metals

| Metal/Element | Crude (ppm) | Ca(OH)$_2$ treated (ppm) | Distilled (ppm) |
|---|---|---|---|
| Boron | 4 | 2 | 3 |
| Calcium | <1 | 134 | <1 |
| Chromium | <1 | <1 | 1 |
| Magnesium | 3 | 4 | <1 |
| Sodium | <3 | <3 | <3 |
| Nickel | <1 | <1 | 1 |
| Phosphorous | 6 | 6 | <1 |
| Lead | 1 | 1 | 1 |
| Silicon | 6 | 6 | 2 |
| Zinc | 1 | 1 | 1 |
| Antimony | <1 | <1 | 1 |

Following metals are <1 ppm: Silver, aluminum, barium, copper, iron, molybdenum, tin, vanadium The calcium hydroxide treatment reduces the total acid number without significantly affecting the impurity profiles of the other components of the composition with the exception of increased calcium. However, the high levels of calcium can be fully removed by other purification methods such as flash distillation.

Example 3

This example describes purification of the crude olefin composition to a purified olefin composition using alumina. This purification method also serves to neutralize the organic acids that are present in the crude olefin composition.

Alumina sorbent is regenerated prior to use by heating at 250° C. for at least two hours. The crude olefin composition is brought to room temperature and is mixed with granular alumina (e.g., Selexsorb CDX) at 10% w/v of the bio-organic compound and mixed overnight. The mixture is then filtered by 0.45 μm filter and treated with 0.01% phenolic antioxidant such as 4-tert-butylcatechol.

When this method is used to purify the farnesene composition from Example 1, the resulting purified farnesene composition has a total acid number of 0 mg KOH/g.

Example 4

This example describes the hydrogenation of limonene in a batch reactor.

Figure 10:
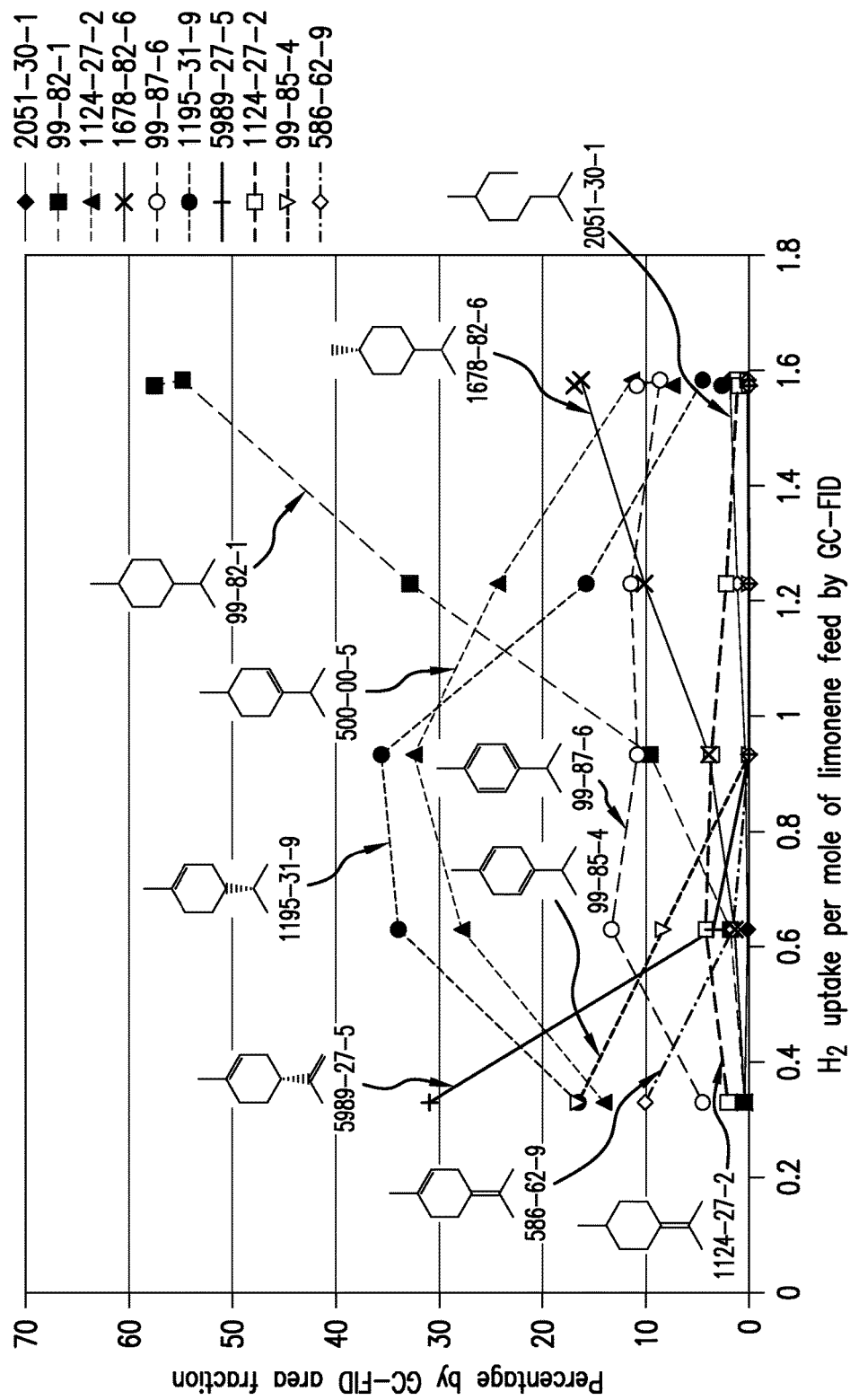
FIG. 10 shows the final product composition from various hydrogenations of limonene in a batch reactor.

Twenty five mL samples of limonene (FloraChem, >98% limonene) were hydrogenated to various extents in batch reactors at 100° C. and 50 psig, over 50 mg 5% Pd/C (Alfa Aesar). Six samples were hydrogenated to various extents, and the compositions of the products are shown in FIG. 10, as determined by GC analysis. As shown by FIG. 10, the composition shifts from less saturated to more-saturated species as the reaction progresses. The final product composition in this example after "complete" saturation was primarily two isomers of p-menthane, with ~9% p-cymene and ~1% dimethyloctane. The concentration of aromatic p-cymene in the "saturated" product of limonene hydrogenation has been found to be a function of catalyst type, temperature, pressure, and reaction time or LHSV (for flow reactors). The results are shown in FIG. 10.

Example 5

This example describes the hydrogenation of limonene in a fixed bed reactor using a palladium catalyst.

Limonene (FloraChem, >98% limonene) was blended with p-menthane or p-menthane/p-cymene mixtures to dilute the feed to 5-50% limonene, and was fed to a fixed bed of 1 L of 0.3% Pd/Al$_2$O$_3$ extrudate obtained from Johnson-Matthey, at flow rates of 21-82 g/min. This is approximately equivalent to a reactor LHSV of ~1.6-6.2 L liquid/L cat/h or process LHSV of ~0.06-0.9 L limonene/L cat/h. The liquid feed was fed at room temperature, and warmed as a result of heat of reaction. The liquid feed and hydrogen were blended and fed to the top of a tubular reactor, so that it was operated in concurrent downflow. Tempered water at 80° C. was added to the middle section of the reactor to maintain the maximum temperature in the reactor at 150° C. or less. The reactor pressure was maintained at 50-90 psig. The excess hydrogen in the reactor effluent was maintained at 3.6-6.5 slpm. The product compositions are shown in Table 5.

TABLE 5 limonene hydrogenation products

| Reactive feed concentration | Feed flow rate g/min | LHSV | Pressure psig | Dimethyl octane | p-menthane | p-menthene | p-cymene | limonene |
|---|---|---|---|---|---|---|---|---|
| 5% | 21 | 1.6 | 50 | | | | | |
| 10% | 21 | 1.6 | 50 | 0.7% | 89% | 0.3% | 9.2% | 0.3% |
| 15% | 21 | 1.6 | 50 | 0.8% | 84% | 1.2% | 13.2% | |
| 20% | 24 | 1.8 | 50 | 0.9% | 87% | | 11.0% | |
| 25% | 24 | 1.8 | 50 | 1.0% | 86% | | 12.0% | |
| 30% | 24 | 1.8 | 50 | 0.9% | 85% | | 13.1% | |
| 35% | 24 | 1.8 | 50 | 0.9% | 83% | | 14.6% | |
| 35% | 24 | 1.8 | 50 | 0.9% | 83% | | 15.0% | |
| 43% | 24 | 1.8 | 50 | 1.0% | 80% | | 17.7% | |
| 50% | 24 | 1.8 | 50 | 1.0% | 78% | 0.7% | 20.0% | |
| 25% | 24 | 1.8 | 50 | 1.0% | 86% | | 12.0% | |
| 25% | 41 | 3.1 | 50 | 0.9% | 81% | 0.2% | 17.0% | |
| 25% | 64 | 4.8 | 50 | 1.0% | 78% | 0.9% | 19.0% | |
| 25% | 82 | 6.2 | 50 | 0.9% | 74% | 2.9% | 21.0% | |
| 25% | 82 | 6.2 | 90 | 1.0% | 79% | 0.6% | 18.0% | |

Example 6

This example describes the hydrogenation of limonene in a fixed bed reactor using a nickel catalyst.

Limonene (FloraChem, >98% limonene) was blended with p-menthane or p-menthane/p-cymene mixtures to dilute the feed and was fed to a fixed bed of 1 L of 20% Ni Al$_2$O$_3$ extrudate obtained from Johnson-Matthey. Feed concentration of limonene was 13-50%, and feed flow rate was 30-104 g/min. The reactor LHSV was 2.3-7.8 L liquid/L cat/h, and the process LHSV was 0.3-2.0 L limonene/L cat/h. Tempered water was added to the center section of the reactor to maintain the maximum temperature at 150° C. or less. Reactor pressures of 50-310 psig were utilized, and hydrogen effluent flow rate was maintained at 2.5-6.5 slpm. The product composition is shown below as a function of operating conditions. The product composition was substantially different than what was observed for 0.3% Pd/Al$_2$O$_3$. As shown in Table 6, measured p-cymene concentration was zero in almost all of the cases shown, demonstrating aromatic hydrogenation activity, since the recycled liquid feed diluent contained p-cymene at the beginning of the test series. No olefinic unsaturated species were observed in the tests shown.

TABLE 6

Limonene product compositions

| Reactive feed concentration | Feed flow rate g/min | LHSV | Pressure Psig | Dimethyl octane | p-menthane | p-menthene | p-cymene | limonene |
|---|---|---|---|---|---|---|---|---|
| 13% | 30 | 2.3 | 50 | 1.2% | 99% | | | |
| 25% | 30 | 2.3 | 50 | 1.1% | 99% | | | |
| 35% | 30 | 2.3 | 50 | 1.2% | 99% | | | |
| 50% | 30 | 2.3 | 50 | 1.2% | 99% | | | |
| 25% | 40 | 3.0 | 55 | 1.1% | 98% | | | |
| 25% | 78 | 5.9 | 58 | 1.1% | 99% | | | |
| 25% | 104 | 7.8 | 47 | 1.1% | 92.0% | | 6.5% | |
| 25% | 100 | 7.5 | 101 | 1.1% | 99% | | | |
| 25% | 100 | 7.5 | 200 | 1.1% | 99% | | | |
| 25% | 99 | 7.4 | 310 | 1.1% | 99% | | | |

Mass balance tests were performed during hydrogenation while using 1 L of 20% Ni/Al$_2$O$_3$ extrudate obtained from Johnson-Matthey, while feeding 60 g/min of 25% limonene/p-menthane. This corresponds to a reactor LHSV of 4.5 L liquid/L cat/h or a process LHSV of 1.1 L limonene/L cat/h. Reactor pressure was maintained at 45-55 psig, temperature was maintained at <150° C., and excess hydrogen in the reactor effluent was maintained at 5.5-7.0 slpm. Mass of the feed liquid was recorded repeatedly before and after operation for several hours. Mass of liquid recovered from the reactor effluent during the same time period was recorded. A mass increase of 0.76% is expected for complete hydrogenation of 25% limonene/p-menthane. The results are shown in the Table 7.

TABLE 7

| | MB1 | MB2 | MB3 | MB4 | SUM |
|---|---|---|---|---|---|
| feed start | 11250 | 16300 | 9700 | 11960 | |
| feed end | 2500 | 2110 | 2080 | 2500 | |
| Processed | 8750 | 14190 | 7620 | 9460 | 40020 |
| Recovered | 8870 | 14680 | 7610 | 9670 | 40830 |
| mass increase | 120 | 490 | −10 | 210 | 810 |
| | | | overall mass increase | | 2.02% |

The overall observed mass increase was 2.0%. The difference between expected and observed mass increase was probably due primarily to error caused by temporal variations in liquid holdup within the reactor system. This observed mass increase indicates that there was no measurable loss of liquid feed mass to side reactions such as hydrocracking.

Example 7

This example describes the hydrogenation of farnesene on a pilot scale.

Microbial-derived farnesene, which had been distilled with a wiped-film distillation apparatus, and which was stabilized with 100 ppmw 4-tert-butylcatechol ("p-TBC"), was fed to a fixed bed reactor in cocurrent downflow with excess hydrogen. The fixed bed reactor contained 1 L of 20% $Ni/Al_2O_3$ extrudate obtained from Johnson-Matthey. The liquid feed rate was 9.6 L/h, and the liquid composition was 10-15% farnesene in recycled farnesane. The reactor LHSV was 9.6 L liquid/L cat/h, and the process LHSV was 0.96 to 1.4 L farnesene/L cat/h. The reactor jacket was maintained at 150° C. by heat transfer fluid. The reactor was maintained at 500 psig. Excess hydrogen flow in the effluent was maintained at >1 slpm. GC analysis showed no measurable residual olefins in the product. Br index measurement was performed by Intertek Caleb Brett according to ASTM D2710, and results for samples from two 5-gal carboys of product yielded measured Br indices of only 8 and 10 mg Br/100 g liquid, indicating that residual unsaturation was negligible.

57 N m3 $H_2$/m3 liquid feed, or 350 scf $H_2$/bbl liquid. Measurements of the effluent gas indicated that it contained approximately 2.2 vol % $H_2S$, corresponding roughly to complete removal of the 1.2 wt % S from the feed liquid. The effluent gas also contained approximately 0.1 vol % propane and heavier hydrocarbon fragments, corresponding to a total loss of ~0.1% of the liquid feed to hydrocracking side reactions.

After 72 hours on stream, the liquid feed stream was switched from unfinished diesel to a sample containing 5 wt. % farnesene (in unfinished diesel). Reactor temperature and pressure were maintained at 340° C. and 650 psig, and the hydrogen:oil ratio was held constant at 300 N m3 $H_2$/m3 liquid feed (1,500 scf $H_2$/bbl liquid). The reactor was run for 120 hours under these conditions. The farnesene-containing sample was desulfurized from 1.2 wt % S down to 25-32 ppmw S during the course of the 120 hours test. The S content in the effluent appeared to be drifting upwards slowly during the test from 25 to 32 ppmw, and no effort was made to decrease the S content of the effluent by adjusting operating conditions. The Br number of the farnesene-containing sample prior to hydroprocessing was substantially higher than that of unfinished diesel alone due to the

TABLE 8

Hydrogenation Conditions

| Time | Liquid feed flow rate (L/h) | Feed concentration (L farnesene/ L Liquid feed) | Process LHSV (L farnesene/ L cat/h) | Reactor LHSV (L liquid/L cat/h) | Hydrogen feed rate (slpm) | Temperature (° C.) Bath SP | 1(top) | 2 | 3 | 4 | 5 | 5 (bot) | Pressure (psig) Upstream | Downstream | Sample # |
|---|---|---|---|---|---|---|---|---|---|---|---|---|---|---|---|
| 9:15 | 9.6 | 10% | 0.96 | 9.6 | 7 | 150 | 128 | 195 | 174 | 164 | 158 | 150 | 503 | 500 | 2 |
| 10:25 | 9.6 | 10% | 0.96 | 9.6 | 7 | 150 | 118 | 202 | 180 | 168 | 160 | 151 | 503 | 500 | 3 |
| 14:20 | 9.6 | 15% | 1.44 | 9.6 | 10 | 150 | 123 | 233 | 193 | 174 | 163 | 150 | 503 | 500 | 7 |
| 15:20 | 9.6 | 15% | 1.44 | 9.6 | 10 | 150 | 124 | 231 | 192 | 173 | 162 | 150 | 503 | 500 | 8 |
| 16:21 | 9.6 | 15% | 1.44 | 9.6 | 10 | 150 | 124 | 241 | 195 | 175 | 163 | 152 | 503 | 500 | 9 |
| 21:26 | 9.6 | 15% | 1.44 | 9.6 | 10 | 150 | 140 | 246 | 195 | 173 | 162 | 151 | 504 | 501 | 38 |
| 22:19 | 9.6 | 15% | 1.44 | 9.6 | 10 | 150 | 140 | 246 | 195 | 173 | 162 | 151 | 503 | 500 | 39 |
| 23:16 | 9.6 | 15% | 1.44 | 9.6 | 10 | 150 | 140 | 246 | 195 | 173 | 162 | 151 | 503 | 500 | 40 |

Example 8

This example describes the hydroprocessing of 5% farnesene with an unfinished diesel fuel containing 1.1 wt. % sulfur. The unfinished diesel contained 1.2 wt. % (12,000 ppmw) S, 100 ppmw N, and approximately 31 wt. % aromatics. The 10%-90% boiling range was 210° C.-370° C. based on simulated distillation.

A NiMoS catalyst (Albemarle) was activated by sulfiding with dimethyldisulfide. To establish a baseline, unfinished diesel was introduced to the reactor at LHSV=2.3, and was processed at 340° C. and 650 psig. Hydrogen was fed with the liquid feed at an $H_2$/oil ratio of 300 N m3 $H_2$/m3 liquid feed (1,500 scf H2/bbl liquid). The reactor temperature profile and gas effluent composition were monitored, and the sample of unfinished diesel was processed for 72 hours. The sample of unfinished diesel was desulfurized from 12,000 ppmw S to 13-20 ppmw S under these processing conditions, and was denitrogenated from 100 ppmw N to 0.3-0.4 ppmw N. The Br number of the feed decreased from 1.4 to <0.5 in the process, and total aromatics content decreased from about 31 wt % to about 21 wt %. Aromatics reduction was substantial for di- and tri-aromatics, and negligible for mono-aromatics. The total hydrogen consumption was about presence of 5% farnesene, and was measured as 9.9. The Br number of the farnesene-containing sample was decreased to <0.5 during the hydroprocessing, and complete conversion of farnesene to saturated C15 was observed with serial GC×GC analysis. The hydrogen consumption increased from the 57 N m3 $H_2$/m3 liquid feed (350 scf $H_2$/bbl liquid) observed for the unfinished diesel sample to 66 N m3 $H_2$/m3 liquid feed (400 scf $H_2$/bbl liquid) for the farnesene-containing sample, due to the additional hydrogen requirement for farnesene hydrogenation. Co-processing the farnesene had no measurable impact on hydrodenitrogenation activity or hydrodearomatization activity, as the effluent concentrations of N and aromatics were approximately the same for both samples. There was no measurable change in hydrocracking activity based on effluent gas concentrations of propane and C6+ species between the two samples. In addition, hydrocracking losses remained constant at about 0.1% for both samples.

The NiMoS catalyst was removed and examined for carbon deposits after both samples were hydroprocessed. Elemental analysis showed concentrations of 7.3 wt % C and 12.1 wt % S, typical values observed for NiMoS hydroprocessing catalysts. This result indicated that there was no substantial increase in carbon deposition onto the catalyst from hydroprocessing the farnesene-containing sample.

Example 9

This example describes the performance of hydrogenation catalyst PRICAT NI HTC500RP 1.2 mm.

The reactor was charged with 25 cm3 PRICAT Ni HTC500RP 1.2 mm catalyst in 4 discrete beds separated by coarse SiC (0.5-1.1 mm) again the catalyst interparticle void was filled with fine grade SiC (0.1-0.3 mm, 0.6 gSiC.$g_{cat}^{-1}$).

The catalyst was activated under the following reduction conditions:
Gas: H2 (100%)
Gas flow rate: 50 l.hr-1
Pressure: 40 psig
Temperature: Ambient –120° C. (5° C.min-1)
120° C. (60 min dwell)
120-230° C. (1.67° C.min-1)
230° C. (60 min dwell)
Cool to first reaction temperature.

The catalyst performance at various temperatures and LHSVs of 5% farnesene in decane (at 500 psig) are summarized in Table 9.

TABLE 9

Bromine index of reactor exit samples from various hydrogenation runs.

| Temperature | LHSV 10 Bromine Index | LHSV 20 | LHSV 40 |
|---|---|---|---|
| 100 | — | 2300 | 4200 |
| 140 | — | 750 | 2400 |
| 175 | <100 | 200 | 800 |
| 220 | — | <100 | 170 |

Gas samples were also taken and analyzed to investigate what, if any, cracking reactions occurred. Table 10 summarizes the results.

TABLE 10

Gas analysis in ppm

| Process Conditions | | Reactor Exit - Gas Analysis (ppm) | | | | |
|---|---|---|---|---|---|---|
| Temp (° C.) | LHSV (hr$^{-1}$) | Methane | Ethane | Propane | Butane | Pentane |
| 175 | 10 | 4607 | 28 | 52 | 32 | 10 |
| 99 | 20 | 84 | 4 | 10 | 18 | 10 |
| 141 | 20 | 368 | 7 | 8 | 15 | 10 |
| 175 | 20 | 1950 | 18 | 37 | 30 | 10 |
| 175 | 20 | 2087 | 18 | 35 | 29 | 10 |
| 175 | 20 | 2181 | 16 | 35 | 27 | 10 |
| 220 | 20 | 6194 | 85 | 121 | 53 | 11 |
| 100 | 40 | 61 | 4 | 9 | 17 | 10 |
| 140 | 40 | 249 | 6 | 7 | 13 | 8 |
| 175 | 40 | 1499 | 15 | 31 | 28 | 10 |
| 175 | 40 | 1597 | 13 | 27 | 23 | 9 |
| 220 | 40 | 4808 | 57 | 97 | 48 | 10 |

Modifying the feed to 5% farnesene in farnesane made little difference in the bromine index of the resulting product at the reactor's exit. It was determined that hydrogenation under the following conditions: 175° C., LHSV 20 hr-1, 500 psig, and 5% farnesene feed resulted in a product with a bromine index of 200-300 with a mono-olefin content <0.5%. In addition, the catalyst showed no significant change in bromine index at standard conditions after 350 hrs on-line under these conditions.

Example 10

The discharged catalyst in Example 9 was characterized to see how the catalyst had been modified. The catalyst was discharged in three portions—top, middle, and bottom of the reactor. The top and middle samples were analyzed by TGA to determine the decomposition temperature of the carbon species. Results show no loss of nickel from the catalyst and no significant loss of nickel surface area. A small amount of sulfur has been observed on the top and middle samples at 0.06 and 0.1% respectively. For both samples, all of the weight loss was observed before 500° C., with the maximum weight loss at around 300° C. which is indicative of a long chain hydrocarbon. No carbon build was observed (e.g. no coking) on the discharged catalyst, however up to 4 wt % hydrocarbon was found which was attributed to long chain hydrocarbons and which were not removable by extraction.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A hydrogenated composition derived from a microbial derived olefin composition, the hydrogenated composition produced by a method comprising:
   (a) separating immiscible olefin from a mixture comprising an aqueous solution, microbial cells and immiscible olefin, thereby forming a crude olefin composition;
   (b) purifying the crude olefin composition thereby forming a purified olefin composition;
   (c) adding a phenolic antioxidant to the purified olefin composition to form a stabilized purified microbial-derived olefin composition, wherein the phenolic antioxidant is a phenol derivative containing an unfused phenyl ring with one or more hydroxyl substituents, and is present in an amount that is at least 0.0001% by weight of stabilized purified microbial-derived olefin composition; and
   (d) reacting the stabilized purified microbial-derived olefin composition with hydrogen in the presence of a hydrogenation catalyst at a temperature at or greater than about 20° C. such that hydrogen saturates at least one double bond in the olefin, thereby producing the hydrogenated composition.

2. The hydrogenated composition of claim 1, wherein the method further comprises adding a phenolic antioxidant to the crude olefin composition.

3. The hydrogenated composition of claim 1, wherein the purification step comprises removing or reducing monoglycerides, diglycerides, ergosterol, squalene, or any combination thereof from the crude olefin composition.

4. The hydrogenated composition of claim 1, wherein the phenolic antioxidant is selected from the group consisting of 3-tert-butyl-4-hydroxyanisole; 2-tert-butyl-4-hydroxyanisole; 2,4,-dimethyl-6-tert-butylphenol; and 2,6-di-tert-butyl-4-methylphenol.

5. The hydrogenated composition of claim 1, wherein the phenolic antioxidant is a catechol.

6. The hydrogenated composition of claim 1, wherein the phenolic antioxidant is 4-tert-butyl catechol.

7. The hydrogenated composition of claim 1, wherein the phenolic antioxidant is present in at least about 0.001% by weight of the stabilized purified microbial-derived olefin composition.

8. The hydrogenated composition of claim 1, wherein the phenolic antioxidant is present in at least about 0.005% by weight of the stabilized purified microbial-derived olefin composition.

9. The hydrogenated composition of claim 1, wherein the phenolic antioxidant is present in at least about 0.01% by weight of the stabilized purified microbial-derived olefin composition.

10. The hydrogenated composition of claim 1, wherein the hydrogenation reaction occurs at a temperature that is greater than about 100° C.

11. The hydrogenated composition of claim 1, wherein the hydrogenated composition comprises a partially hydrogenated immiscible olefin.

12. The hydrogenated composition of claim 1, wherein the microbial-derived olefin is a $C_5$-$C_{20}$ isoprenoid.

13. The hydrogenated composition of claim 1, wherein the microbial-derived olefin is a $C_{10}$-$C_{15}$ isoprenoid.

14. The hydrogenated composition of claim 1, wherein the stabilized purified microbial-derived olefin comprises farnesene in at least about 50%, 60%, 70%, 80%, 90%, 93%, 95%, 97%, 99% or greater by weight of the immiscible olefin.

15. The hydrogenated composition of claim 14, wherein the hydrogenation reaction comprises selective hydrogenation of farnesene to reduce one, two, three, or four double bonds in farnesene.

16. The hydrogenated composition of claim 15, wherein farnesene is selectively hydrogenated to reduce one double bond.

17. The hydrogenated composition of claim 15, further comprising bisabolane in an amount that is equal to or greater than 0.1% by weight of the hydrogenated composition.

18. A hydrogenated composition derived from a microbial-derived olefin composition, the hydrogenated composition produced by a method comprising:
   reacting a stabilized purified microbial-derived olefin composition with hydrogen in the presence of a hydrogenation catalyst, wherein the stabilized purified microbial-derived olefin composition comprises:
   (a) farnesene in an amount that is at least equal to or greater than about 90% by weight of the stabilized purified microbial-derived olefin composition;
   (b) bisabolene in an amount that is equal to or greater than about 0.1% by weight of the stabilized purified microbial-derived olefin composition;
   (c) zingibrene in an amount that is equal to or greater than about 0.1% by weight of the stabilized purified microbial-derived olefin composition; and
   (d) a phenolic antioxidant, wherein the phenolic antioxidant is a phenol derivative containing an unfused phenyl ring with one or more hydroxyl substituents in an amount that is at least about 0.005% by weight of the stabilized purified microbial-derived olefin composition,
   wherein the hydrogenation reaction saturates at least one double bond in farnesene.

19. The hydrogenated composition of claim 18, wherein the hydrogenated composition further comprises at least about 0.1% bisabolane by the weight of the hydrogenated composition.

20. The hydrogenated composition of claim 18, wherein the hydrogenated composition comprises a partially hydrogenated farnesene.

* * * * *